United States Patent
Chen et al.

(10) Patent No.: US 11,773,510 B2
(45) Date of Patent: Oct. 3, 2023

(54) METHOD OF DISCOVERING SPECIFIC FUNCTIONAL ANTIBODIES

(71) Applicant: GENEWIZ SUZHOU, Jiangsu (CN)

(72) Inventors: Weizhi Chen, Jiangsu (CN); Xin Wu, Jiangsu (CN); Wang Wang, Jiangsu (CN); Zhongping Sun, Jiangsu (CN); Guojuan Liao, Jiangsu (CN)

( * ) Notice: Subject to any disclaimer, the term of this patent is extended or adjusted under 35 U.S.C. 154(b) by 394 days.

(21) Appl. No.: 16/064,264

(22) PCT Filed: May 24, 2017

(86) PCT No.: PCT/CN2017/085668
§ 371 (c)(1),
(2) Date: Jun. 20, 2018

(87) PCT Pub. No.: WO2017/206773
PCT Pub. Date: Dec. 7, 2017

(65) Prior Publication Data
US 2019/0233813 A1    Aug. 1, 2019

(30) Foreign Application Priority Data

Jun. 1, 2016   (CN) .......................... 201610382201.1

(51) Int. Cl.
*C40B 30/04* (2006.01)
*C40B 40/08* (2006.01)
(Continued)

(52) U.S. Cl.
CPC ............ *C40B 40/08* (2013.01); *C07K 16/005* (2013.01); *C07K 16/1018* (2013.01);
(Continued)

(58) Field of Classification Search
CPC ................ C12N 15/10; C12N 15/1062; C12N 15/1089; C12N 15/1096; G16B 15/00;
(Continued)

(56) References Cited

U.S. PATENT DOCUMENTS 7,858,308 B2 * 12/2010 Cibelli et al. ..................... 435/6
10,450,368 B2 * 10/2019 Haynes et al. ...... C07K 16/1063
(Continued)

FOREIGN PATENT DOCUMENTS

| CN | 103003697 A | 3/2013 |
| CN | 103184216 A | 7/2013 |

(Continued)

OTHER PUBLICATIONS

Yu, X., "Current applications of high-throughput DNA sequencing technology in antibody drug research" Acta Pharmacetica Sinica (2012) 47(3):322-331 [Abstract].
Wang, X., et al., "Overview of high-throughput sequencing analysis of B-cell BCR CDR3 receptor library" Chinese Journal of Immunology (2011) 27:947-954 [Abstract].
International Search Report, PCT/CN2017/085668, dated Aug. 18, 2017.
(Continued)

*Primary Examiner* — Christian C Boesen
(74) *Attorney, Agent, or Firm* — Robert C. Netter, Jr.; Dann, Dorfman, Herrell & Skillman

(57) ABSTRACT

The invention relates to a method for discovering specific functional antibodies, in particular to a method for discovering specific functional antibodies based on sequence composition and frequency analysis of variable regions of immune host antibodies. Compared with conventional high-throughput antibody sequencing method, this method can quickly and accurately obtain the full-length sequence of the variable region of antibody containing candidate CDR3, the success rate of antibody gene pairing is high and it is suitable for the detection of few samples, and improves the efficiency of obtaining specific functional antibodies.

14 Claims, 3 Drawing Sheets
Specification includes a Sequence Listing.

(51) Int. Cl.
| | |
|---|---|
| *C07K 16/18* | (2006.01) |
| *C07K 16/00* | (2006.01) |
| *C12N 15/10* | (2006.01) |
| *C07K 16/10* | (2006.01) |
| *G16B 15/00* | (2019.01) |
| *G16C 20/60* | (2019.01) |
| *G16B 35/00* | (2019.01) |
| *C40B 50/06* | (2006.01) |

(52) U.S. Cl.
CPC .......... *C07K 16/1081* (2013.01); *C07K 16/18* (2013.01); *C12N 15/10* (2013.01); *C12N 15/1062* (2013.01); *C12N 15/1089* (2013.01); *C12N 15/1096* (2013.01); *G16B 15/00* (2019.02); *C07K 2317/10* (2013.01); *C07K 2317/21* (2013.01); *C07K 2317/565* (2013.01); *C07K 2317/567* (2013.01); *C40B 30/04* (2013.01); *C40B 50/06* (2013.01); *G16B 35/00* (2019.02); *G16C 20/60* (2019.02)

(58) Field of Classification Search
CPC ...... G16B 35/00; C07K 16/18; C07K 16/005; C07K 16/1018; C07K 16/1081; C40B 40/08; C40B 50/06; G16C 20/60
See application file for complete search history.

(56) References Cited

U.S. PATENT DOCUMENTS

| | | | |
|---|---|---|---|
| 10,550,430 B2 * | 2/2020 | Sahin et al. | ......... C12Q 1/6881 |
| 2011/0312505 A1 * | 12/2011 | Reddy et al. | ..................... 506/2 |
| 2013/0296535 A1 * | 11/2013 | Church et al. | ..... C12N 15/1065 |

FOREIGN PATENT DOCUMENTS

| | | |
|---|---|---|
| CN | 103215255 A | 7/2013 |
| CN | 106047857 A | 10/2016 |
| WO | 2011146514 A2 | 11/2011 |
| WO | 2013078455 A2 | 5/2013 |

OTHER PUBLICATIONS

Weinstein, J.A., et al., "High-throughput Sequencing of the Zebrafish Antibody Repertoire" Science (2009) 324(5928):807-810.

Menzel, U., et al., "Comprehensive Evaluation and Optimization of Amplicon Library Preparation Methods for HighThroughput Antibody Sequencing". PLoS One (2014) 9(5):e96727.

Reddy, S.T., et al., "Monoclonal antibodies isolated without screening by analyzing the variable-gene repertoire of plasma cells" Nature Biotech. (2010) 28(9):965-969.

Wang, X., et al., "Primary Analysis of IgG & IgM H Chain CDR3 Repertoire of the Volunteers Vaccinated Against HBV, by 454 High-Throughput Sequencing Technology" 8th Congress of the Chinese Society for Immunology (2012) pp. 302-303.

* cited by examiner

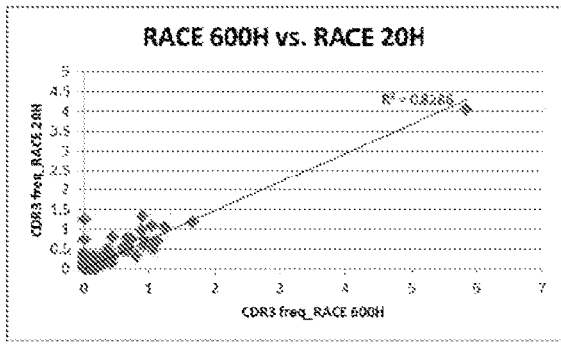 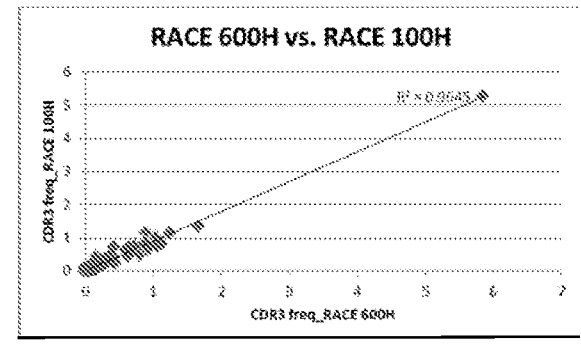
FIG. 3(a)      FIG. 3(b)
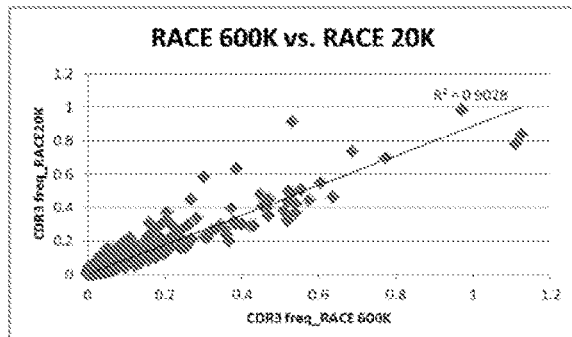 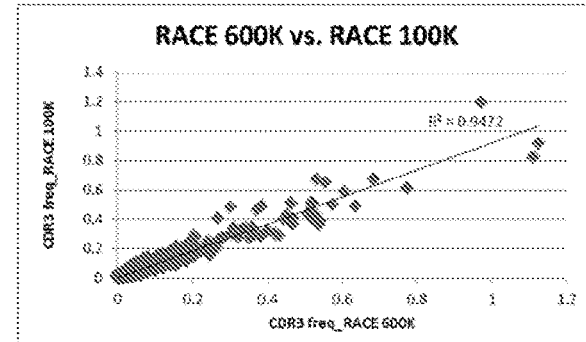
FIG. 3(c)      FIG. 3(d)
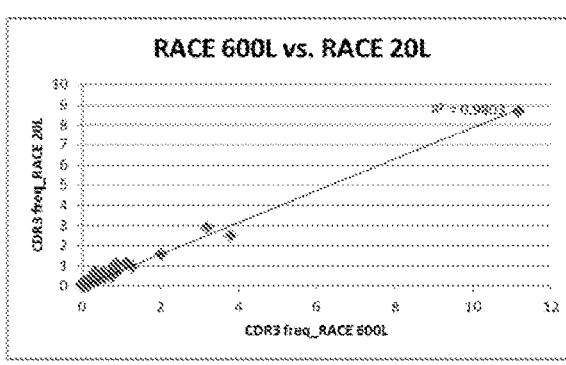 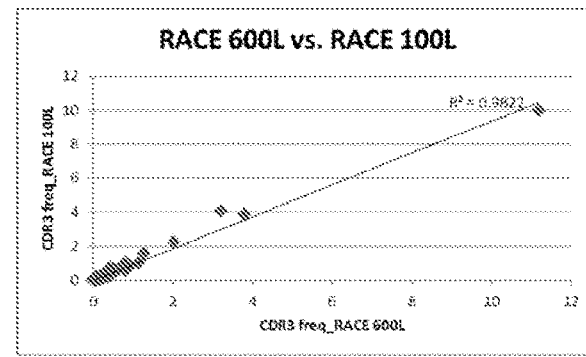
FIG. 3(e)      FIG. 3(f)
FIG. 3

DENV-2 virus

FIG. 4

Flu Virus

METHOD OF DISCOVERING SPECIFIC FUNCTIONAL ANTIBODIES

CROSS-REFERENCE TO RELATED APPLICATIONS

This application is A § 371 of International Application No. PCT/CN2017/085668, filed May 24, 2017, which claims priority from Chinese Patent Application No. 201610382201.1, filed Jun. 1, 2016. The entire disclosure of each of the aforesaid applications is incorporated by reference in the present application.

TECHNICAL FIELD OF THE INVENTION

The invention relates to the biotechnology field, in particular to a method of discovering specific functional antibodies, in particular to a method of discovering specific functional antibodies based on the composition and frequency analysis of variable regions of immune host antibodies.

BACKGROUND TECHNOLOGY OF THE INVENTION

A completely identical antibody produced by a single B-cell and only against a specific antigen epitope is called a monoclonal antibody. Since Kohler and Milstein reported that hybridoma techniques were used to obtain monoclonal antibodies against sheep erythrocytes in 1975, more and more monoclonal antibodies have been widely used in the fields of detection of medical diagnosis and separation of biomolecules and others. Because of their strong specificity, high purity and good uniformity, monoclonal antibodies have improved the efficiency and accuracy of medical testing. In recent years, with the development of tumor immunotherapy, monoclonal antibodies against immune checkpoint show a great prospect in tumor immunotherapy.

In addition to hybridoma techniques, many techniques have been applied to the production of monoclonal antibodies, such as vitro display techniques represented by phage display, single cell cloning techniques, EB virus-mediated B cell immortalization techniques, protein spectrum analysis combined with DNA high-throughput sequencing techniques etc. These techniques have their own strong points and weakness, for example, hybridoma techniques are limited to a limited variety such as mice or rabbits, and the subsequent isolation of monoclonal hybridoma is time-consuming and huge work. The production of monoclonal antibodies is unstable and easy to be lost. The in vitro display techniques also require a long period and the generated antibodies are the same as hybridoma antibodies which need to be humanized.

The method of antibody discovery based on high-throughput sequencing developed in recent years reveals the variation of specific antibody abundance in antibody gene spectrum under specific immune status by comparing the frequency of CDR3 sequences in host antibody gene spectrum before and after immunization. The full-length sequence of CDR3 sequence with the largest frequency variation is selected for functional validation using in vitro pairing expression as a candidate sequence of specific antibodies. This method is not limited to species. A large number of candidate pairs can be generated from the antibody gene spectrum in a short period for functional verification. It is possible to obtain antibodies with high affinity.

The characteristics of second generation sequencing, such as reading length, accuracy, throughput, cost performance and so on, are suitable for studying the diversity of antibody library composition, but there are some technical difficulties in antibody sequencing library construction, high throughput antibody sequencing and data analysis etc. As a result, the obtained antibody gene spectrum information is inaccurate, the contained antibody gene information is biased, it is difficult to accurately define the variation of CDR3 frequency, and the verification efficiency of vitro pairing function of the selected full-length genes is low.

Second generation sequencing has been widely used to study the diversity of the composition of antibody gene spectrum. However, how to avoid the introduction of biases in the sequencing library construction is always a difficult problem. At present, RT or RACE methods are frequently used to construct high-throughput antibody sequencing library. RT method designs primers and amplifies the variable regions of antibody according to the conserved sequences of known variable regions of antibody sequences. Because of the very high sequence diversity of antibody genes, multiple primers or merger primers are frequently used to amplify the multiple PCR in the real operation, in order to cover the antibody genes to the maximum extent. However, multiple primer amplification, sample RNA degradation, incomplete database and so on inevitably introduce biases in library construction and data analysis. As a result, the results of sequencing cannot truly reflect the composition and changes of the variable regions of antibody. Another difficulty in constructing RACE library is that the requirements of quality and quantity of sample RNA are high. However, it is difficult to obtain enough samples in practical work; in particular, the number of clinicopathological samples is often difficult to meet the needs of RACE library construction.

SUMMARY

According to the shortcomings of the prior arts and the actual requirements, the invention provides a method of discovering specific functional antibodies. The method can roundly study the composition and distribution of the variable regions of multi-species antibody genes without bias.

For this purpose, the invention adopts the following technical scheme:

The invention provides a method of discovering specific functional antibodies, including the following steps:

(1) Extract the total RNAs of at least one target antigen immunize host subject and construct a high-throughput antibody sequencing library;

(2) The high-throughput sequencing library constructed by step (1) is used for high-throughput sequencing of the variable regions of the immunoglobulin gene, and the gene spectrum of variable regions of antibody for the at least one target antigen is obtained;

(3) Candidate CDR3 and corresponding heavy chain and light chain antibody nucleic acid sequences are selected as candidate pairing sequences from the variable region gene spectrum of antibody; and (4) The light chain and heavy chain genes are selected to pairwise express in vitro to produce candidate recombinant antibodies.

Among them, the selection of candidate CDR3 from the gene spectrum of the variable regions of antibody includes the analysis of the results of high-throughput sequencing of Read1 and/or Read2 separately, select candidate CDR3 homologous clusters, and combine with the results of Read1 and Read2 splicing, the full-length gene of the variable regions of antibody containing this CDR3 homologous cluster is identified.

In the invention, the result of Read1 and/or Read2 and the result of Read1 and Read2 splicing are analyzed.

As the preferably technical scheme, the method of constructing high-throughput antibody sequencing library described in step (1) is RACE library construction and/or RT library construction, such as single RACE library construction, single RT library construction or both RACE library construction and RT library construction at the same time.

Preferably, the RACE library construction includes the following steps:

(a) Obtain the cells of the subjects and isolate the total RNA;

(b) Use oligo (dT) as primer and total RNA in step (a) as template, synthesize cDNAs by reverse transcription; and (c) Use cDNA produced in step (b) as template, the high-throughput antibody sequencing library is constructed by using the amplicon library construction method after using the two-step PCR amplification method or the first step PCR method to amplify the antibody genes.

The invention constructs the RACE libraries of the heavy chain, Kappa chain and Lambda chain respectively, uses the Illumina system to sequence the library, to sequence the heavy chain library separately, and to, separately or in combination, sequence the Kappa and Lambda chain libraries.

In the invention, the optimized two-step PCR amplification is used to construct the library, which can reduce the RNA input volume of the sample to 20 ng, simplify the construction process of the library, and maintain the coverage degree and accuracy of the obtained gene spectrum of the variable regions of antibody.

Preferably, the RT library construction includes the following steps:

(a') Obtain the cells of the subjects and isolate the total RNA;

(b') Use oligo(dT) as primer and total RNA in step (a') as template, synthesize cDNAs by reverse transcription; and (c') Use cDNA produced in step (b') as template, specific primers are used to amplify the antibody genes, and then the PCR amplified products are constructed DNA library.

In the invention, the PCR amplified program in the RACE library construction and RT library construction is as follows:

① 95° C.2 min;
② 95° C. 30 sec, Tm 30 sec, 72° C. 30 sec; 15-35 cycles
③ 72° C. 7 min;
④ 4° C. store Preferably, the subjects described in the step (a) of the RACE library construction should be any or at least two combinations of mammals, amphibians, fish or birds.

Preferably, the mammals should be any or at least two combinations of humans, mice, primates, rabbits, goats, sheep or pigs.

Preferably, the cells described in the step (a) of the RACE library construction should be derived from any or at least two combinations of the peripheral blood, lymphoid organs, spleen, bone marrow or liver of the subjects.

Preferably, the cells described in the step (a) of the RACE library construction should include any or at least two combinations of memory B cells, plasma cells, or plasmablast.

Preferably, the primers of PCR used in the first round of two-step PCR amplification described in step (c) of RACE library construction include forward primer and reverse primer. The forward primer contains partial forward joint sequence and sequence as shown by SEQ ID NO.1. The reverse primer contains a partial reverse joint sequence and a sequence as shown in one of the SEQ ID NO. 2-4;

```
SEQ ID NO. 1:
AAGCAGTGGTATCAACGCAGAGTA;

SEQ ID NO. 2:
GGAAGACCGATGGGCCCTTGGTGG;

SEQ ID NO. 3:
GCAGGCACACAACAGAGGCAGTTCCAG;

SEQ ID NO. 4:
CACACCAGTGTGGCCTTGTTGGCTT
```

The forward primers used in the first round of PCR in the two-step PCR amplification described in the step (c) of the RACE library construction are as follows:

Partial joint sequence—SEQ ID NO.1: AAGCAGTGGTATCAACGCAGAGTA (The forward primer is from Clontech SMARTer RACE 5'/3' Kit).

As an example, the reverse primers used in the first round of PCR in the two-step PCR amplification described in the step (c) of the RACE method can adopt below three modes:

Partial joint sequence—SEQ ID NO.2: GGAAGACCGATGGGCCCTTGGTGG (heavy chain IgG reverse primer);

Partial joint sequence—SEQ ID NO.3: GCAGGCACACAACAGAGGCAGTTCCAG (kappa reverse primer);

Partial joint sequence—SEQ ID NO.4: CACACCAGTGTGGCCTTGTTGGCTT (lambda reverse primer).

Preferably, the partial forward joint sequence includes 5-60 bp of the 3' end of the Illumina forward joint primer, and the partial reverse joint sequence includes 5-60 bp of the 3' end of the Illumina reverse joint primer.

Preferably, the sequence of the Illumina forward joint primer is shown by SEQ ID NO.5, and the Illumina reverse joint primer is shown by SEQ ID NO.6.

```
SEQ ID NO. 5:
AATGATACGGCGACCACCGAGATCT

ACACTATAGCCTACACTCTTTCCCTACAC

GACGCTCTTCCGATCT;

SEQ ID NO. 6:
CAAGCAGAAGACGGCATACGAGATA

GCTTCAGGTGACTGGAGTTCAGACGTGT

GCTCTTCCGATCT.
```

Preferably, the primers used in the second round of PCR in the two-step PCR amplification described in the step (c) of the RACE library construction are conventional Illumina library construction primers.

Preferably, the high-throughput sequencing is composed by any or at least two combinations of sequencing by synthesis, sequencing by joining, sequencing by hybridization, single molecule DNA sequencing, multiple polymerase community sequencing or nano-pore sequencing, then selected as sequencing by synthesis, and further selected as Illumina platform sequencing.

In the invention, using Illumina Miseq 2×300 sequencing system, although the antibody variable region gene sequence is long, it can basically reach the upper limit of Illumina sequencing, but compared with other high-throughput sequencing methods such as Roche 454, Illumina Miseq 2×300 system is with high accuracy, high throughput and low cost; compared with the third generation sequencing method, although it does not have the strong point in reading long, but the strong points of Illumina system in throughput and sequencing cost are obviously.

In the invention, the analysis method adopts the method of two-end sequencing and then selecting, which makes up for the deficiency of the reading length of Illumina sequencing, and the full-length sequence can be obtained more accurately by two-end sequencing.

In the invention, it is difficult for the existing Illumina Miseq 2×300 system to ensure the full length of the antibody variable region. An optimized selected method of full-length of the antibody variable region is developed, and the full-length sequence of the antibody variable region is obtained by combining the results of RACE and RT library construction and sequencing, and the bias due to incomplete data can be reduced.

Preferably, the principle of selecting candidate CDR3 is: any or at least two combinations of high frequency sequence after CDR3 clustering, selection of CDR3 sequences with significantly higher frequency after immunization or outbreak phase than in pre-immunization or convalescence phase, or the sequence of V gene family corresponding to CDR3 after immunization or outbreak phase significantly different from that in the pre-immunization or convalescence phase.

Preferably, the selection of candidate CDR3 in the step (3) and corresponding heavy chain and light chain antibody nucleic acid sequences as candidate pairing sequence includes the following steps:

(1') Select candidate CDR3 homologous clusters;

(2') Anchor the CDR3 homology cluster, and the full length amino acid sequences of the high frequency antibody heavy chain and the light chain variable region containing the CDR3 homology cluster are selected as the first and second pairing candidate sequences in the gene spectrum of the variable region of antibody;

(3') Determine nucleic acid sequences of first and second pairing candidate sequences;

Preferably, the selection in the step (2') of the full-length amino acid sequences of the high-frequency antibody heavy chain and the light chain variable region containing this candidate CDR3 homologue cluster includes the following steps: all the Read1 and Read2 of the CDR3 homologous cluster are selected from the gene spectrum of antibody variable region to compare the antibody database and get the most frequent amino acid sequences in CDR region and FR region; at the same time, the sequence results of Read1 and Read2 are spliced, and all the spliced sequences are compared with the antibody database to determine the highest frequency amino acid sequences in the CDR region and FR region; compare and combine the amino acid sequences of CDR region and FR region obtained from two sources, obtain the full-length amino acid sequence of the variable region of antibody corresponding to the CDR3 homology cluster as the candidate pairing sequence, and select the corresponding full-length nucleotide sequences of the highest frequency variable region in the Read1 and Read2 spliced sequences.

Preferably, the full-length nucleotide sequence of the variable region described in step (3') is compared with the sequence of the highest frequency antibody variable region containing specific CDR3 homology cluster obtained by RT library construction, and the full-length sequence of the variable region of antibody is obtained as a candidate pairing sequence.

In the invention, for the partial antibody variable region, due to the inclusion of a longer CDR region, FR region or a longer 5'UTR region, the splicing rate is very low, so it is difficult to obtain the full length sequence of the high frequency variable region by the method of sequentially selection with the locking of CDR3. The invention adopts RT method to construct library at the same time to make up for the problem of low splicing rate of RACE library.

In the invention, the method of obtaining full-length antibody by combining RACE library sequencing and RT library sequencing is as follows: parallel use RACE library construction sequencing and RT library construction sequencing for the same sample, compare the consistency of high-frequency CDR3 in the two libraries, lock CDR3 when the consistency achieves a certain standard, and select the highest frequency DNA sequence containing the CDR3 in the RT library.

Preferably, the method also includes the identification of selected antibodies.

Preferably, the identification includes the identification of the obtained antibody with at least one target antigen.

Preferably, the identification steps include scFv or Fab fragments or IgG of the antibody obtained by expressing in vitro, and the resultant scFv, Fab fragments or IgG with the target antigen are made binding force test.

Preferably, the vitro expression method is to express scFv or Fab fragments through the display method of prokaryotic cells, phages or yeast systems, or to express Fab or IgG through the exogenous gene of mammalian cells.

Preferably, the test methods include, but are not limited to, ELISA and/or SPR.

Compared with the prior arts, the invention has the following beneficial effects:

(1) The analysis method of the invention adopts the method of two-end sequencing and splicing then selecting, which makes up for the deficiency of the reading length of the Illumina sequencing, and the full-length sequence can be obtained more accurately by the two-end sequencing;

(2) The invention adopts the optimized two-step PCR amplification library construction, which can reduce the RNA input amount of the sample to 20 ng, simplify the construction process of the library, and maintain the coverage degree and accuracy of the acquired variable region gene spectrum of the antibody;

(3) The invention aims at the existing Illumina Miseq 2×300 system which is difficult to obtain the full length of the variable region of antibody, develops an optimized method of selecting the full length of the variable region of antibody, obtain the full-length sequence of the variable region of antibody by combining with the results of RACE and RT library construction sequencing, and reduces bias due to incomplete data; and (4) The discovery method for specific antibodies in the invention is simple, fast and low cost, can detect micro samples, and makes a foundation for the discovery of a large number of antibodies.

BRIEF DESCRIPTION OF THE DRAWINGS

FIG. 3 is the correlation analysis of antibody gene CDR3 frequency of different RNA inputs: FIG. 3(a) is the comparison of heavy-chain CDR3 when RNA input is 600 ng and 20 ng; FIG. 3(b) is the comparison of heavy chain CDR3 when RNA input is 600 ng and 100 ng; FIG. 3(c) is the comparison of kappa CDR3 when RNA input is 600 ng and 20 ng; FIG. 3(d) is the comparison of kappa CDR3 when RNA input is 600 ng and 100 ng; FIG. 3(e) is the comparison of lambda CDR3 when RNA input is 600 ng and 20 ng; FIG. 3(f) is the comparison of lambda CDR3 when RNA input is 600 ng and 100 ng.

FIG. 4 is a pairing expression result of a candidate dengue virus antibody of the embodiment 2 in the invention.

FIG. 5 is a pairing expression result of a candidate flu virus antibody of the embodiment 3 in the invention.

FIG. 6 is the correlation analysis of CDR3 frequency of RT and RACE libraries: FIG. 6(a) is the correlation analysis of the CDR3 frequency of heavy chain in RT and RACE libraries; FIG. 6(b) is the correlation analysis of CDR3 frequency of Lambda chain in RT and RACE libraries.

SPECIFIC IMPLEMENTATIONS

In order to further elaborate the technical means adopted by the invention and its effect, the technical scheme of the invention is further explained by combining with the drawings and by concrete embodiments, but the invention is not limited to the scope of the embodiment.

Figure 1:
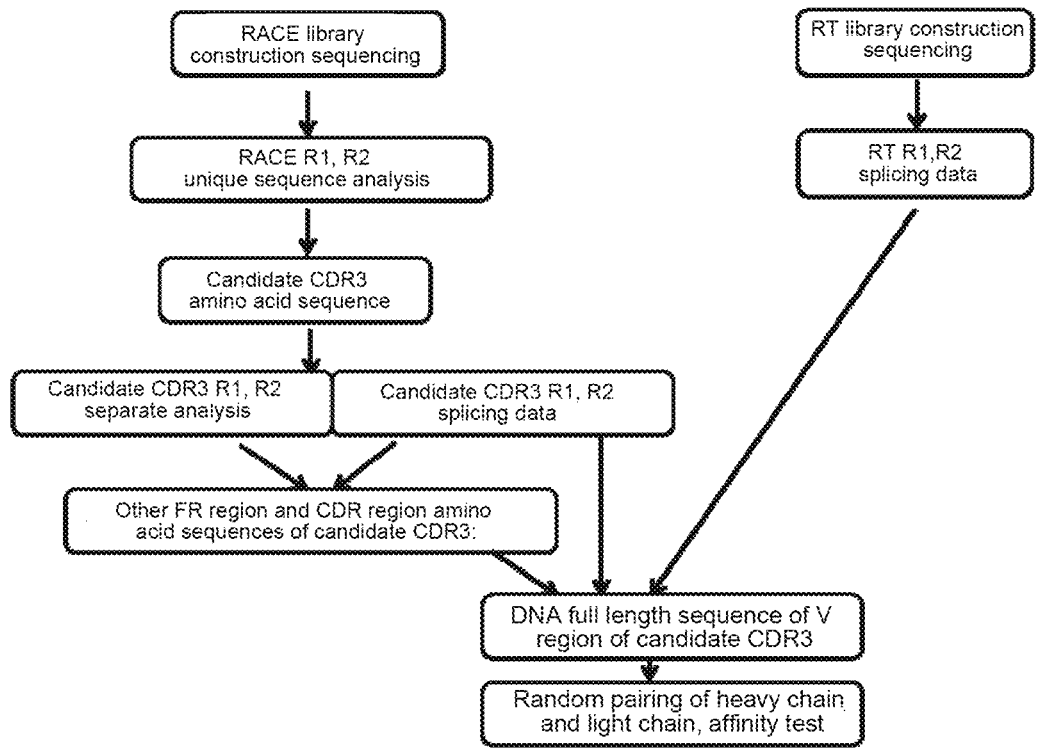
FIG. 1 is a schematic diagram of the optimized discovery method for antibodies in the invention.
Figure 2:
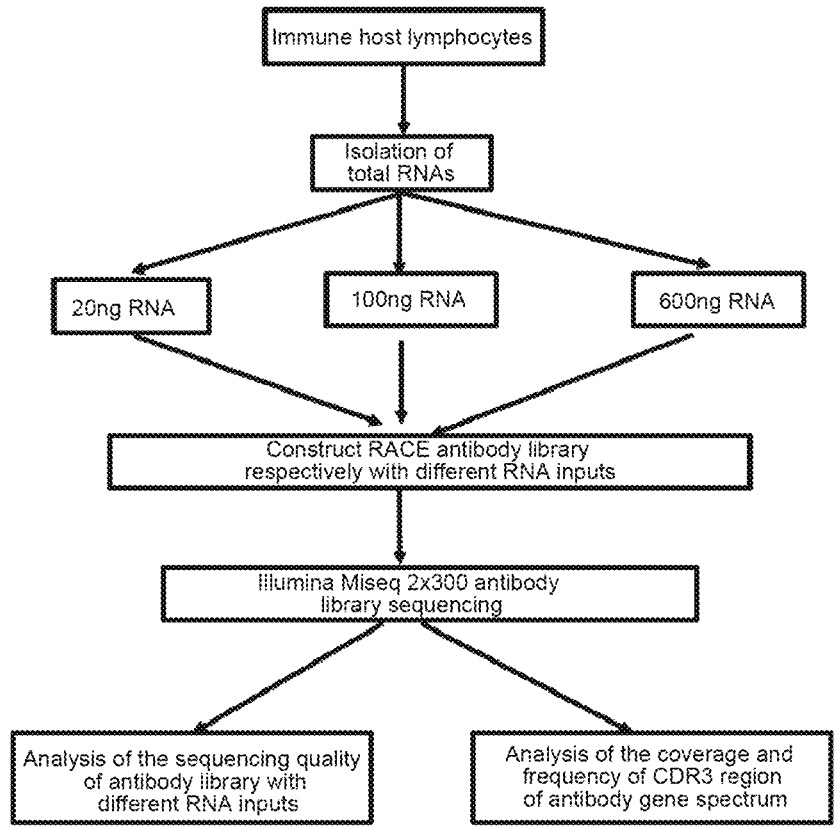
FIG. 2 is a schematic diagram of concrete steps of the embodiment 1 of the invention.

Embodiment 1 an Optimized High-Throughput Library Construction Method for Few Samples The concrete steps to build the library are shown in FIG. 2. Sample preparation and first chain cDNA synthesis: Peripheral blood mononuclear cells (PBMC) are isolated from human or animal peripheral blood by density gradient centrifugation. Total RNAs are isolated from PBMC by Trizol. 20 ng, 100 ng and 600 ng RNAs are used as template and oligo (dT) is used as primer for the synthesis of first-chain cDNA. The concrete operation can be carried out by referring to the manual of SMARTer® RACE 5'/3' Kit.

The optimized two-step PCR method is used to construct the antibody library. In the first round of PCR amplification, the forward primer is the optimized SMARTer® RACE 5'/3' Kit UPM with the partial joint primer containing Illumina, the reverse primer containing the sequence of the invariant region of the antibody and the partial joint primer containing Illumina. VH, VK and VL are amplified respectively. The reaction system is as follows:

| | Reaction System | |
|---|---|---|
| | Component | Volume |
| PCR reaction | 1 × TransStart ® FastPfu Fly Buffer | 5 μL |
| | Optimized UPM | 5 μL |
| | Reverse primer | 0.2 μL |
| | TransStart ® FastPfu Fly DNA Polymerase | 0.5 μL |
| | cDNA | 5 μL |
| | dNTPs | 0.2 mM |
| | Total volume | 50 |

PCR reaction conditions are as follows:

| | Reaction program | Cycles number |
|---|---|---|
| Amplification program | 95° C. 2 min | 1 |
| | 95° C. 30 s | 25 |
| | 67° C.-62° C. 30 s | |
| | 72° C. 30 s | |
| | 72° C. 7 min | 1 |

The first round of PCR products are recovered by magnetic beads.

The primer of the second round of PCR is conventional Illumina library construction primer, and the reaction system is as follows:

| | Reaction System | |
|---|---|---|
| | Component | Volume |
| PCR reaction | 1 × TransStart ® FastPfu Fly | 5 μL |
| | Forward primer | 0.2 μM |
| | Reverse primer | 0.2 μM |
| | TransStart ® FastPfu Fly DNA Polymerase | 0.5 μL |
| | First round PCR recovered product | 20 μL |
| | dNTPs | 0.2 mM |
| | Total volume | 50 |

PCR reaction conditions are as follows:

| | Reaction program | Cycles number |
|---|---|---|
| Amplification program | 95° C. 2 min | 1 |
| | 95° C. 30 s | 6-8 |
| | 60° C. 30 s | |
| | 72° C. 30 s | |
| | 72° C. 7 min | 1 |

The steps of gel cutting and purification of products can be referred to the manual of QIAquick Gel Extraction Kit. After the library is constructed, Bioanalyzer High Sensitivity DNA chip is used for QC, sequencing platform is Illumina Miseq 2×300, the result is shown in FIG. 3(a)-(f).

The results of FIG. 3(a)-(f) show that the frequency correlation R2 values of heavy chain, Kappa chain and Lambda chain CDR3 are 0.83, 0.90 and 0.98 respectively at the 20 ng RNA input, comparing with 600 ng RNA input, it shows a high correlation. And the figure shows the ranking of high frequency CDR3, For example, CDR3, which ranks the top 10 in the gene spectrum of the variable region of antibody, also shows a high consistency at 600 ng, 100 ng and 20 ng RNA inputs. The comparison of CDR3 frequency correlation explains that the RACE library constructed with 20 ng RNA input can meet the requirements of antibody library sequencing in terms of antibody gene coverage and CDR3 region bias.

Embodiment 2 an Optimized Antibody Gene Screening Method for Dengue Virus Monoclonal Antibody Use the method of RACE antibody library construction described in embodiment 1, total RNAs are isolated from PBMC of dengue patients in acute stage and convalescence stages, and construct the RACE libraries of heavy chain, Kappa chain and Lambda chain respectively. Use Illumina Miseq 2×300 system to sequence the library: the heavy chain library is sequenced alone, and the Kappa and Lambda chain libraries are combined and sequenced. The sequencing results are processed by software Trimmomatic-0.30, the parameters are set as follows: phred33, LEADING:20, TRAILING:20, SLIDINGWINDOW:20:20, MINLEN: 200). Remove poor quality data. The following improvements are made to data analysis. Comparing the data amount in the antibody library after removing and preserving Singleton sequence, it is found that the data amount changes greatly after Singleton is removed, so Singleton sequence cannot be removed. And the way of repeated sequence normalization can reduce the occupation of server resources: first, find out each sequence and its repeat times, then analyze each sequence by IgBlast, and obtain each CDR3 frequency by counting the repeat times.

TABLE 1

Comparison of data amount of antibody library before and after removing Singleton sequence

|  | Reads amount before removing singleton | Reads amount after removing singleton |
|---|---|---|
| 6H-R1 | 30179 | 4573 |
| 6H-R2 | 30179 | 471 |
| 6K-R1 6L-R1 | 574845 | 141848 |
| 6K-R2 6L-R2 | 574845 | 16785 |

TABLE 2

Comparison of data amount of antibody library before and after repeated sequence normalization

|  | Reads amount before repeated sequence normalization | Reads amount after repeated sequence normalization |
|---|---|---|
| 6H-R1 | 30179 | 27278 |
| 6H-R2 | 30179 | 29913 |
| 6K-R1 6L-R1 | 574845 | 463091 |
| 6K-R2 6L-R2 | 574845 | 563921 |

TABLE 3

Comparison of library quality of dengue patients in acute and convalescent stages

| Library | Sequence amount | Sequence amount after organization | Q30 index after organization |
|---|---|---|---|
| Convalescent stage H | 2365300 | 812294 | 81.90 |
| Convalescent stage K | 1569720 | 647412 | 82.88 |
| Convalescent stage L | | | |
| Acute stage H | 4721106 | 60358 | 83.98 |
| Acute stage K | 1726272 | 1149690 | 82.45 |
| Acute stage L | | | |

Because CDR3 sequences are almost unique markers for different antibody genes, the abundance of CDR3 sequences can be evaluated in the gene spectrum of the variable region of antibodies according to the number of obtained CDR3 sequences. The sequences of FR region and CDR region are determined according to IgBlast website, but the sequence of CDR3 region is not determined by IgBlast website, so we use characteristic sequence of FR4 region to determine CDR3 amino acid sequence, and the characteristic sequence of heavy chain FR4 initiation region is WG*G (SEQ ID NO.199) or GQG (SEQ ID NO.200), characteristic sequences of Kappa and Lambda chains are FG*GT (SEQ ID NO:201). Run IgBlast respectively for the Read1 and Read2 sequences and merge the results, and select the pairing candidate CDR3 sequence based on one or all of the following principles: 1) High frequency sequence after CDR3 clustering; 2) Select the CDR3 sequences which have significantly higher frequency in after-immunization or outbreak stage than in the pre-immunization or convalescent stage; 3) The V gene family corresponding to CDR3 is significantly different between that of after-immunization or outbreak stage and that of pre-immunization or convalescent stage.

The CDR3 frequency changes of heavy chain and light chain of dengue patients in acute and convalescent stages are shown in tables 4, 5 and 6. The results show that the concentration of CDR3 in acute stage is significantly higher than that in convalescent stage, indicating that it may be related to specific antigen.

TABLE 4

Analysis of the CDR3 frequency of heavy chain of dengue patients in the acute and convalescent stages

| Heavy chain CDR3 sequence | Frequency of acute stage (%) | Frequency of convalescent stage (%) | CDR3 Cluster (%) |
|---|---|---|---|
| ARALSEKSLTTSYLDC (SEQ ID NO. 7) | 8.53 | 0.11 | 9.76 |
| VKDASTTSIGAAPFDY (SEQ ID NO. 8) | 5.97 | 0.03 | 10.04 |
| THRRPSLRYPDV (SEQ ID NO. 9) | 5.45 | 0.15 | 5.62 |
| ASLGGTVTDAFDL (SEQ ID NO. 10) | 3.13 | 0.03 | 5.55 |
| AKDASTTSKGAAPFDY (SEQ ID NO. 11) | 2.49 | 0 | 3.14 |
| ARGFTYGHYFDY (SEQ ID NO. 12) | 2.23 | 0 | 2.24 |
| VKDASTTSIGAAPFDN (SEQ ID NO. 13) | 2.05 | 0 | 10.04 |
| AKTVVTAPGVFDY (SEQ ID NO. 14) | 1.86 | 0 | 2.15 |
| ASDILDAFDV (SEQ ID NO. 15) | 1.84 | 0 | 1.85 |
| VKDASTTSIGAAPFDS (SEQ ID NO. 16) | 1.72 | 0 | 10.04 |
| ASLGGTVTDAFDV (SEQ ID NO. 17) | 1.21 | 0 | 5.55 |

TABLE 4 -continued

Analysis of the CDR3 frequency of heavy chain of dengue patients in the acute and convalescent stages

| Heavy chain CDR3 sequence | Frequency of acute stage (%) | Frequency of convalescent stage (%) | CDR3 Cluster (%) |
|---|---|---|---|
| ASLGGTVTDAFDI (SEQ ID NO. 18) | 1.15 | 0 | 5.55 |
| ATGYTYGYYFDY (SEQ ID NO. 19) | 1.00 | 0 | 1.01 |

TABLE 5

Analysis of CDR3 frequency of Kappa chain of dengue patients in the acute and convalescent stages

| Kappa chain CDR3 sequence | Frequency of acute stage (%) | Frequency of convalescent stage (%) | CDR3 Cluster (%) |
|---|---|---|---|
| QQANSFPWT (SEQ ID NO. 20) | 5.94 | 0.06 | 6.31 |
| HQYSSWPPGGT (SEQ ID NO. 21) | 4.87 | 0.18 | 5.22 |
| HQYNSWPPGGT (SEQ ID NO. 22) | 2.83 | 0 | 3.04 |
| HQYNAWPPGGT (SEQ ID NO. 23) | 2.81 | 0 | 3.78 |
| MQGTHWRS (SEQ ID NO. 24) | 2.63 | 0 | 2.68 |
| QQYSFWPWT (SEQ ID NO. 25) | 2.45 | 0 | 2.56 |
| QQYDSFPLT (SEQ ID NO. 26) | 1.68 | 0 | 1.75 |
| QQANNFPWT (SEQ ID NO. 27) | 1.57 | 0 | 1.66 |
| HQYTSWPPGGT (SEQ ID NO. 28) | 1.28 | 0 | 1.37 |
| QQRSNWPRT (SEQ ID NO. 29) | 1.24 | 0.01 | 1.3 |
| QQISNFPIT (SEQ ID NO. 30) | 1.17 | 0 | 1.2 |
| QQSFSPPWT (SEQ ID NO. 31) | 1.09 | 0.07 | 1.17 |
| QQSGSSLH (SEQ ID NO. 32) | 1.02 | 0 | 1.27 |
| QQRSTWPYT (SEQ ID NO. 33) | 1 | 0.07 | 1.09 |

TABLE 6

Analysis of CDR3 frequency of Lambda chain of dengue patients in the acute and convalescent stages

| Lambda chain CDR3 sequence | Frequency of acute stage (%) | Frequency of convalescent stage (%) | CDR3 Cluster (%) |
|---|---|---|---|
| CSYAASYYDTGV (SEQ ID NO. 34) | 10.08 | 1.06 | 10.96 |
| SSYRSISPFYV (SEQ ID NO. 35) | 5.2 | 0.64 | 5.45 |
| SSYRSSSPFYV (SEQ ID NO. 36) | 5.06 | 0.52 | 5.18 |
| QVWDRSTNHRV (SEQ ID NO. 37) | 4.49 | 0.97 | 4.53 |
| QVWDRSSDHRL (SEQ ID NO. 38) | 3.69 | 0.61 | 3.82 |
| QSYDTSLRAGV (SEQ ID NO. 39) | 3.58 | 0.65 | 3.67 |
| SSYTGSSTV (SEQ ID NO. 40) | 2.06 | 0.19 | 2.06 |
| LLSYGGAPCV (SEQ ID NO. 41) | 1.5 | 0.27 | 1.58 |
| CSYAGRSTWV (SEQ ID NO. 42) | 1.48 | 0.04 | 1.53 |
| QSFDDSLSGWV (SEQ ID NO. 43) | 1.38 | 0.24 | 1.4 |
| QVWDRSTNHRL (SEQ ID NO. 44) | 1.26 | 0.15 | 1.28 |
| CSYAGSNTWI (SEQ ID NO. 45) | 1.24 | 0.21 | 2.55 |
| CSYAGSNTWV (SEQ ID NO. 46) | 1.16 | 0.17 | 2.55 |

Anchor candidate CDR3 sequences, take the heavy-chain CDR3 sequence THRRPSLRYPDV (SEQ ID NO.9) as an example, run all Read2 and corresponding Read1 containing the CDR3 homology cluster respectively by IgBlast to obtain the amino acid sequences of CDR region and FR region, such as CDR1, CDR2, CDR3, FR1, FR2, FR3 and FR4. The results of IgBlast analysis are combined into the R12 file. In parallel, the sequencing results of R1 and R2 are spliced, and the amino acid and nucleotide sequences of each domain are determined by running IgBlast with the spliced sequences, and the Contig file is obtained.

The selection of the full length sequence of the variable region follows the following steps: taking the heavy chain CDR3-THRRPSLRYPDV (SEQ ID NO.9) homologous cluster as an example, the highest frequency variable region of the antibody gene is screened and obtained from the R12 file. The amino acid sequences of each domain are as follows, as shown in Table 7:

```
                                    (SEQ ID NO. 48)
FR1(QITLKESGPMLVKPTQTLTLTCTFS)-

(SEQ ID NO. 47)
CDR1(GFSLSTSGVG)-
```

-continued

FR2(VGWIRQPPGEALEWLAI)- (SEQ ID NO. 51)

CDR2(IYWDDDK)- (SEQ ID NO. 52)

FR3(RYSPSLRSRLTISKDTSKNQVVLTMTNLDPVDTATYFC) (SEQ ID NO. 49)

FR4(WGQG). (SEQ ID NO. 50)

Further, the corresponding nucleotide sequences are selected in turn from the Contig file according to the sequence of nnFR4-nnCDR3-nnFR3-nnCDR2-nnFR2-nnCDR1-nnFR1-contig. The corresponding full-length nucleotide sequence of the antibody variable region of the highest frequency nucleotide sequence is obtained, which should contain the complete FR and CDR regions and the signal peptide sequence.

TABLE 7

Heavy chain CDR3 THRRPSLRYPDV (SEQ ID NO. 9) homologous clusters corresponding to combinations of the highest frequency FR and CDR regions Heavy chain-THRRPSLRYPDV-R12 highest frequency amino acid sequence

| | |
|---|---|
| CDR1 | GFSLSTSGVG (SEQ ID NO. 47) |
| FR1 | QITLKESGPMLVKPTQTLTLTCTFS (SEQ ID NO. 48) |
| FR3 | RYSPSLRSRLTISKDTSKNQVVLTMTNLDPVDTATYFC (SEQ ID NO. 49) |
| FR4 | WGQG (SEQ ID NO. 50) |
| FR2 | VGWIRQPPGEALEWLAI (SEQ ID NO. 51) |
| CDR2 | IYWDDDK (SEQ ID NO. 52) |

Take Kappa chain -HQYSSWPPGGT (SEQ ID NO.21) homologous cluster as an example, the most abundant sequence combinations of FR and CDR regions ae screened and obtained from the R12 file. The amino acid sequence of each region is as follows: FR1(EIVMTQSPATLSVSPGER-ATLSCRAS) (SEQ ID NO.54)-FR2 (LAWYQHKPGQAPRLLLY) (SEQ ID NO.57)-FR3 (TRAAGIPDRF SGSGSGTEFTLTIS SLQSEDFAVYFC) (SEQ ID NO.55)-CDR2(GAS) (SEQ ID NO.58)-CDR1 (QSVSSN) (SEQ ID NO.53)-FR4(FGQGT) (SEQ ID NO.56), refer to FIG. 8. The corresponding highest frequency nucleotide sequence is selected in turn from the Contig file according to the sequence of nnFR4-nnCDR3-nnFR3-nnCDR2-nnFR2-nnCDR1-nnFR1-contig, the corresponding highest frequency full-length DNA sequence of the antibody variable region is obtained.

TABLE 8

Kappa chain CDR3 HQYSSWPPGGT (SEQ ID NO. 21) homologous clusters corresponding to combinations of the highest frequency FR and CDR regions Kappa-HQYSSWPPGGT-R12 highest frequency amino acid sequence

| | |
|---|---|
| CDR1 | QSVSSN (SEQ ID NO. 53) |
| FR1 | EIVMTQSPATLSVSPGERATLSCRAS (SEQ ID NO. 54) |

TABLE 8-continued

Kappa chain CDR3 HQYSSWPPGGT (SEQ ID NO. 21) homologous clusters corresponding to combinations of the highest frequency FR and CDR regions Kappa-HQYSSWPPGGT-R12 highest frequency amino acid sequence

| | |
|---|---|
| FR3 | TRAAGIPDRFSGSGSGTEFTLTISSLQSEDFAVYFC (SEQ ID NO. 55) |
| FR4 | FGQGT (SEQ ID NO. 56) |
| FR2 | LAWYQHKPGQAPRLLLY (SEQ ID NO. 57) |
| CDR2 | GAS (SEQ ID NO. 58) |

Figures 4, 5, 6A, 6B:
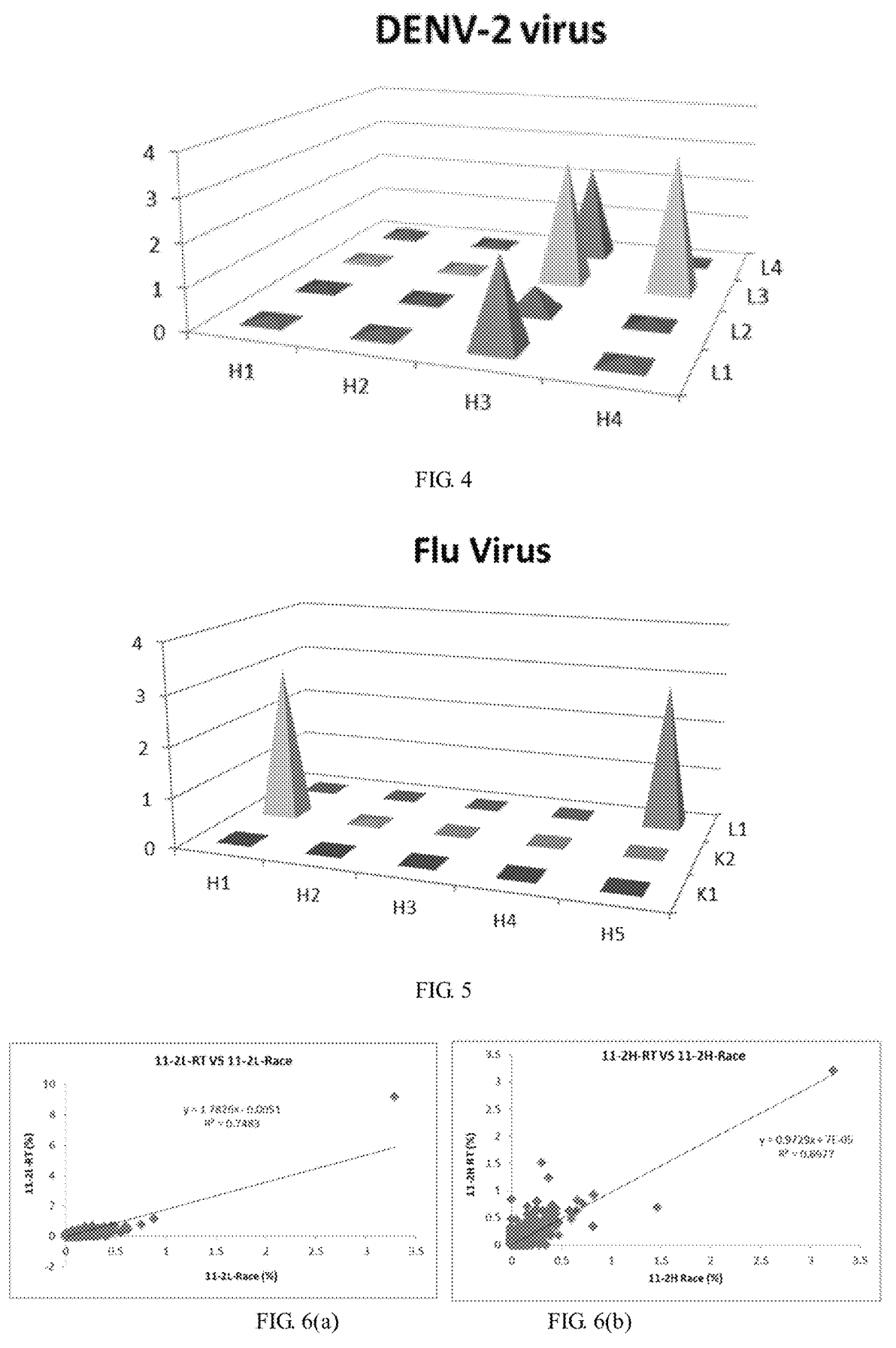

This selecting method of sequence of antibody variable region has the following benefits: while sequencing data are processed, Singleton reads are retained; the splicing rates of variable regions of antibody genes corresponding to different high frequency CDR3 are significantly different, the full length splicing rate of heavy chain high frequency CDR3 sequences in the following table ranges from 34% to 91% (Table 9). If the splicing sequence analysis is used directly, in some cases the data loss may be huge and the CDR3 frequency analysis may even be biased. For current process, R1 and R2 sequences are used for CDR3 composition analysis at first, which avoids the risk of effective data loss and also helpful to obtain accurate frequency of CDR3 sequences; for current process, the highest frequency amino acid sequences information of FR and CDR regions are obtained from R1 and R2 files, and the highest frequency nucleotide sequences of variable region of antibody gene are selected from Contig sequence file, it can effectively guarantee the sequences of variable regions are the highest frequency sequences, and guarantee the integrity and accuracy of the sequence information. A separate selection of sequences of FR and CDR regions in the R12 file also verifies the accuracy of the current process as shown in FIG. 4.

TABLE 9

Analysis of sequencing and splicing of variable region of antibody

| Heavy chain CDR3_Seq | Reads amount | Splicing Reads amount | Splicing rate(%) |
|---|---|---|---|
| ARALSEKSLTTSYLDC (SEQ ID NO. 7) | 2394 | 810 | 33.8 |
| VKDASTTSIGAAPFDY (SEQ ID NO. 8) | 1676 | 730 | 43.6 |
| THRRPSLRYPDV (SEQ ID NO. 9) | 1531 | 1387 | 90.6 |
| ARGFTYGHYFDY (SEQ ID NO. 12) | 628 | 415 | 66.1 |

Analysis of antibody gene pairing and expressing: an expression frame is constructed by overlapping PCR, and the expression frame includes promoter, variable region and antibody constant region. The selected antibody heavy chain gene and light chain gene are combined and paired, then transfected 293FT cells for expression. The supernatant is obtained for Elisa assay and tested for its affinity to antigen. Concrete implementation steps are as follows: The variable regions of candidate heavy chain and light chain are constructed expression frame by using the method of bridging PCR. The expression frame includes promoter, variable region and constant region of human antibody. The plasmids containing heavy chain and light chain expression frames are paired and transfected 293FT cells for vitro expression and antibody analysis. 293T cells are collected, adjusted cell density and inoculated with 48-hole plate to $1.2 \times 10^5$/hole; after cultivation in an incubator at 37° C. and 5% $CO_2$ for overnight, the cells are transfected when the cell density reaches 60-80%. The plasmids of 0.25 ug heavy chain and 0.75 ug light chain are incubated at room temperature for 5 minutes, mixed with the transfection reagent then cultivated at room temperature for 20 min to form the transfection complex. The transfection complex is added into the cell pore and mixed softly, then cultivated in an incubator at 37° C. and 5% CO2 for 72 hours. The supernatant is collected and detected activity by Elisa. First, an anti-human IgG(Fc) and a detection antigen are diluted with pH 9.6 carbonic acid coating solution to 10 μg/mL, 96-well microtiter plate coated with 100 μL at 4° C. for overnight; or at 37° C., 2 hours; then sealed off by 4% skim milk powder-PBS and 300 μL/well, treated for 1~2 h at 37° C. The liquid in microtiter plate is discarded, the rest is washed with PBST for three times, then added transfection and cultivated for 48 hours, the supernatant of 100 μl/well is treated at 37° C. for 1 h. The culture medium and PBS control are set up. The liquid in the microtiter plate is discarded and the rest is washed with PBST for three times, and HRP goat anti-human IgG(Fc) 1: 2000 and HRP goat anti-human IgG 1: 5000 are added respectively. Then 100 μl/well is treated at 37° C. for 1 h. The liquid in the microtiter plate is discarded, the rest is washed with PBST for five times, and the OPD chromogenic solution is added, 100 μL/well, avoid light for coloration; The absorption value of OD490 wavelength is read by Microplate Reader.

Four heavy chains are paired with five Kappa chains and four Lambda chains respectively. Elisa results (FIG. 4) show that there is no positive result in the pairing of kappa chains and heavy chains, and five positive clones are obtained from the pairing of lambda chains and heavy chains. The positive rate is 5/36.

Embodiment 3 an Optimized Antibody Gene Screening Method for Flu Virus Monoclonal Antibody Use the method of RACE antibody library construction described in embodiment 1, total RNAs are isolated from PBMC of volunteers before and 7 days after the injection of influenza vaccine, and construct the RACE libraries of heavy chain, Kappa chain and Lambda chain respectively according to the method described in embodiment 2. Use Illumina Miseq 2×250 system to sequence high-throughput. The methods of data processing, the determination of FR and CDR regions, and the selection of candidate CDR3 amino acid sequences are the same as those described in embodiment 1.

TABLE 10

CDR3 frequency analysis of heavy chain before and after immunization of influenza vaccine

| Heavy chain CDR3_Seq | Frequency on 7th day after immunization (%) | Frequency before immunization (%) | V gene | Frequency change of V gene (%) |
| --- | --- | --- | --- | --- |
| MSWNDRVVAP (SEQ ID NO. 59) | 4.84 | 0.07 | IGHV2-70*13 | 100% |
| SVVSFPPY (SEQ ID NO. 60) | 4.17 | 0.05 | IGHV3-74*01 | 75% |
| EVGGERAY (SEQ ID NO. 61) | 2.88 | 0.06 | IGHV3-7*01 | 25% |
| DRDASGDFDI (SEQ ID NO. 62) | 1.95 | 0.03 | IGHV1-3*01 | 0% |
| APGGQWAY (SEQ ID NO. 63) | 1.21 | 0.01 | IGHV3-7*01 | 25% |
| SSVVSFPPY (SEQ ID NO. 64) | 0.97 | 0.03 | IGHV3-74*01 | 75% |
| DRVTGDNFYYYMGV (SEQ ID NO. 65) | 0.78 | 0.02 | IGHV3-23*01 | 0% |
| GSTIMVTL (SEQ ID NO. 66) | 0.76 | 0.01 | IGHV3-53*01 | 100% |
| LQFFEGRHMDV (SEQ ID NO. 67) | 0.67 | 0 | IGHV2-70*13 | 100% |
| DRVASGDFDI (SEQ ID NO. 68) | 0.47 | 0.02 | IGHV3-23*01 | 0% |
| LLSGGENPSYYYHMDV (SEQ ID NO. 69) | 0.4 | 0.01 | IGHV2-70*01 | 100% |

TABLE 10-continued

CDR3 frequency analysis of heavy chain before and after immunization of influenza vaccine

| Heavy chain CDR3_Seq | Frequency on 7th day after immunization (%) | Frequency before immunization (%) | V gene | Frequency change of V gene (%) |
| --- | --- | --- | --- | --- |
| KTYGSGSFDYFDY (SEQ ID NO. 70) | 0.35 | 0.01 | IGHV4-59*01 | 40% |
| GATVVNDLEY (SEQ ID NO. 71) | 0.33 | 0 | IGHV3-53*01 | 100% |
| GGTIRVTL (SEQ ID NO. 72) | 0.33 | 0.01 | IGHV3-53*01 | 100% |
| MNWNDRVVDP (SEQ ID NO. 73) | 0.33 | 0 | IGHV2-70 | |
| GGTIMVTL (SEQ ID NO. 74) | 0.32 | 0 | IGHV3-53*01 | 100% |
| DYLSGTYTPPLY (SEQ ID NO. 75) | 0.32 | 0 | IGHV1-24*01 | 100% |
| ERGEVGDSVDNFYYYMDV (SEQ ID NO. 76) | 0.28 | 0 | IGHV4-59*01 | 40% |
| PMTYYYDISDAGAYYFDT (SEQ ID NO. 77) | 0.28 | 0.01 | IGHV4-4*02 | 0 |
| PPTAHHFNAFYI (SEQ ID NO. 78) | 0.28 | 0.01 | IGHV4-39*01 | 22% |

TABLE 11

CDR3 frequency analysis of Kappa chain before and after immunization of influenza vaccine

| Kappa chain CDR3_Seq | Frequency on 7th day after immunization (%) | Frequency before immunization (%) | V gene | Frequency change of V gene (%) |
| --- | --- | --- | --- | --- |
| QQRSDWPYT (SEQ ID NO. 79) | 2.993274 | 0.01 | IGKV3-11*01 | -9% |
| QQYDA (SEQ ID NO. 80) | 2.178924 | 0.01 | IGKV1-33*01 | 100% |
| HQSSIRSWT (SEQ ID NO. 81) | 1.560191 | 0.01 | IGKV1-39*01 | 21% |
| LQHNTYPQT (SEQ ID NO. 82) | 1.399475 | 0.01 | IGKV1D-17*02 | 100% |
| QQSSTSSWT (SEQ ID NO. 83) | 1.274091 | 0 | IGKV1-39*01 | 21% |
| QQYNNWPPYT (SEQ ID NO. 84) | 1.19955 | 0.48 | IGKV3-15*01 | -31% |
| MQGKYWPT (SEQ ID NO. 85) | 1.103035 | 0.01 | IGKV2-30*01 | 100% |
| QQYRGSSCT (SEQ ID NO. 86) | 1.060809 | 0 | IGKV3-20*01 | 50% |
| QQYGSSPPWT (SEQ ID NO. 87) | 1.020738 | 0.07 | IGKV3-20*01 | 0.5 |

TABLE 11 -continued

CDR3 frequency analysis of Kappa chain before and after immunization of influenza vaccine

| Kappa chain CDR3_Seq | Frequency on 7$^{th}$ day after immunization (%) | Frequency before immunization (%) | V gene | Frequency change of V gene (%) |
|---|---|---|---|---|
| QQYDYSSST (SEQ ID NO. 88) | 0.998763 | 0 | IGKV3-20*01 | 0.5 |

TABLE 12

CDR3 frequency analysis of Lambda chain before and after immunization of influenza vaccine

| Lambda chain-CDR3_Seq | Frequency on 7$^{th}$ day after immunization (%) | Frequency before immunization (%) | V gene | Frequency change of V gene (%) |
|---|---|---|---|---|
| AAWDDDLSGPV (SEQ ID NO. 89) | 16.83722 | 0.23 | IGLV1-47*01 | 100% |
| AAWDDSQNGPL (SEQ ID NO. 90) | 2.558374 | 0.03 | IGLV1-44*01 | 20% |
| QT (SEQ ID NO. 91) | 1.711464 | 3.48 | IGLV4-69*01 | -100% |
| ATWDDNLSGPV (SEQ ID NO. 92) | 1.589042 | 0.02 | IGLV1-47*01 | 100% |
| QV (SEQ ID NO. 93) | 1.483721 | 0 | IGLV3-21*01 | 100% |
| AAWDDNFSGAEV (SEQ ID NO. 94) | 1.269279 | 0.01 | IGLV1-47*01 | 100% |
| SSYTSSSTPWV (SEQ ID NO. 95) | 1.175902 | 0.05 | IGLV2-14*01/03 | 0% |
| AVWDNSLNGFYV (SEQ ID NO. 96) | 1.161244 | 0.01 | IGLV1-44*01 | 20% |
| AAWDDSLSPPEV (SEQ ID NO. 97) | 1.099626 | 0.01 | IGLV1-47*01/02 | 100% |
| ATWDDDLSGPV (SEQ ID NO. 98) | 1.037193 | 0.01 | IGLV1-47*01/02 | 100% |

The expression frame is constructed by fusion of PCR; the frame includes promoter, variable region and antibody constant region. The selected antibody heavy chain gene and light chain gene are randomly paired and transfected 293FT cells for expression and the supernatant is obtained for Elisa assay, its affinity to antigens is tested.

The concrete methods for expression in vitro can be referred to dengue virus cases. Elisa results show that one functional antibody per pair is obtained from the pairing of candidate Kappa chain and Lambda chain with heavy chain respectively. From FIG. 5, we can see that the success rate of pairing is 2/15.

Embodiment 4 Full-Length Sequences of Variable Region of Antibody Obtained by Combining the Sequencing Results of RACE and RT Libraries The optimized full-length sequence selection method of the variable region described in embodiment 2 may partially make up for the insufficient reading length of the sequence. But for partial antibody variable region, such as containing long length of CDR and FR regions or 5' UTR may lead to low splicing rate. It is difficult to obtain the full length sequence of the high frequency variable region by the described selection in turn method with locking CDR3. For example, in four sequences of highest-frequency CDR3 in Table 9, the corresponding splicing rate of two CDR3 is about 40%.

A method is developed to obtain the full-length sequence of variable region of antibody by combining the results of RACE and RT libraries sequencing. The RACE and RT methods are used to construct library and sequence for the same sample in parallel, and the consistency of high-frequency CDR3 in the two libraries is compared. The CDR3 homology cluster is locked and the maximum frequency variable region full length DNA sequence containing the CDR3 homology cluster is selected from the RT library.

The method of concrete implementation is as follows: The RT method and the RACE method described in embodiment 1 are used to separate RNA from PBMC of blood sample of dengue patient at acute stage; construct heavy chain and light chain libraries by RT method at the same time.

The steps of RT library construction are as follows: According to the method described in the embodiment 1, the first chain of cDNA is obtained, and the specific primers are used to amplify variable regions of heavy chain (VH), Kappa chain (VK) and Lambda chain (VL). The forward primer is designed in the conserved region of the variable region, and the reverse primer is designed in the constant region. The primer sequences are shown in Table 13, in which heavy chain primers are quoted from REF. 1.

Adopt the 25 μL PCR amplification system consisting of 2.2 μM VH or 3.6 μM VK or 2.2 μM VL forward primers, 1 μM reverse primers, 2.5 μL AccuPrime Buffer I(Invitrogen), 2 μL cDNA and 0.75 μL AccuPrime Taq Polymerase.

PCR program: 95° C. 2 min; 25 cycles (95° C. 30 sec, 56° C. 30 sec, 72° C. 1min); 72° C. 7 min; 4° C. The operation steps of gel cutting and purification of PCR products can be referred to the manual of QIAquick Gel Extraction Kit (Qiagen).

The construction of high-throughput sequencing library can be referred to the manual of NEBNext® Ultra™ DNA Library Prep Kit for Illumina (NEB). After the library construction is finished, Bioanalyzer High Sensitivity DNA chip (Agilent) is used for QC and the sequencing platform is Illumina Miseq 2×300.

TABLE 13

List of primers used in RT Library Construction

| | | |
|---|---|---|
| VH chain forward primers | IGHV_LR1 | CGCAGACCCTCTCACTCAC (SEQ ID NO. 99) |
| | IGHV_LR2 | TGGAGCTGAGGTGAAGAAGC (SEQ ID NO. 100) |
| | IGHV_LR3 | TGCAATCTGGGTCTGAGTTG (SEQ ID NO. 101) |
| | IGHV_LR4 | GGCTCAGGACTGGTGAAGC (SEQ ID NO. 102) |
| | IGHV_LR5 | TGGAGCAGAGGTGAAAAAGC (SEQ ID NO. 103) |
| | IGHV_LR6 | GGTGCAGCTGTTGGAGTCT (SEQ ID NO. 104) |
| | IGHV_LR7 | ACTGTTGAAGCCTTCGGAGA (SEQ ID NO. 105) |
| | IGHV_LR8 | AAACCCACACAGACCCTCAC (SEQ ID NO. 106) |
| | IGHV_LR9 | AGTCTGGGGCTGAGGTGAAG (SEQ ID NO. 107) |
| | IGHV_LR10 | GGCCCAGGACTGGTGAAG (SEQ ID NO. 108) |
| | IGHV_LR11 | GGTGCAGCTGGTGGAGTC (SEQ ID NO. 109) |

TABLE 13 -continued

List of primers used in RT Library Construction

| | | |
|---|---|---|
| VH chain reverse primers | HGR | AAGACCGATGGGCCCTTG (SEQ ID NO. 110) |
| VK chain forward primers | kvf1 | TGACCCAGTCTCCATCCTCC (SEQ ID NO. 111) |
| | kvf2 | TGACCCAGTCTCCATCCTCA (SEQ ID NO. 112) |
| | kvf3 | TGACCCAGTCTCCATCCTTCC (SEQ ID NO. 113) |
| | kvf4 | TGACCCAGTCTCCATCCTTACT (SEQ ID NO. 114) |
| | kvf5 | TGACCCAGTCTCCATCTGCC (SEQ ID NO. 115) |
| | kvf6 | TGACCCAGTCTCCATCTTCC (SEQ ID NO. 116) |
| | kvf7 | TGACACAGTCTCCAGCCACC (SEQ ID NO. 117) |
| | kvf8 | TGACACAGTCTCCAGGCACC (SEQ ID NO. 118) |
| | kvf9 | TGACGCAGTCTCCAGGCAC (SEQ ID NO. 119) |
| | kvf10 | TGACCCAGTCTCCAGACTCC (SEQ ID NO. 120) |
| | kvf11 | TGACTCAGTCTCCACTCTCCC (SEQ ID NO. 121) |
| | kvf12 | TGACCCAGTCTCCATTCTCCC (SEQ ID NO. 122) |
| | kvf13 | TGACCCAGACTCCACTCTCTC (SEQ ID NO. 123) |
| | kvf14 | TGACCCAGACTCCACTCTCC (SEQ ID NO. 124) |
| | kvf15 | TGACCCAGTCTCCTTCCACC (SEQ ID NO. 125) |
| | kvf16 | TCACGCAGTCTCCAGCATTC (SEQ ID NO. 126) |
| | kvf17 | TGACGCAGTCTCCAGCCAC (SEQ ID NO. 127) |
| | kvf18 | TGACCCAGTCTCCATCTTCTG (SEQ ID NO. 128) |
| VK chain reverse primers | KCR | ACACAACAGAGGCAGTTCCAG (SEQ ID NO. 129) |
| VL chain forward primers | lvf1 | GGTCCTGGGCCCAGTCTGTCG (SEQ ID NO. 130) |
| | lvf2 | GGTCCTGGGCCCAGTCTGCC (SEQ ID NO. 131) |
| | lvf3 | GTCCTGGGCCCAGTCTGTGCT (SEQ ID NO. 132) |
| | lvf4 | TGTCAGTGGTCCAGGCAGGGC (SEQ ID NO. 133) |
| | lvf5 | GATCCTGGGCTCAGTCTGCCCTG (SEQ ID NO. 134) |
| | lvf6 | GCTCTGAGGCCTCCTATGAGCTG (SEQ ID NO. 135) |
| | lvf7 | GATCCGTGGCCTCCTATGAGCTG (SEQ ID NO. 136) |
| | lvf8 | TCTCTGAGGCCTCCTATGAGCTG (SEQ ID NO. 137) |
| | lvf9 | GCTCTGCGACCTCCTATGAGCTG (SEQ ID NO. 138) |
| | lvf10 | GTTCTGTGGTTTCTTCTGAGCTGAC (SEQ ID NO. 139) |
| | lvf11 | GCTCTGTGACCTCCTATGTGCTG (SEQ ID NO. 140) |
| | lvf12 | TCTCTGTGGCCTCCTATGAGCTG (SEQ ID NO. 141) |
| | lvf13 | GTTCTGTGGCCTCCTATGAGCTG (SEQ ID NO. 142) |
| | lvf14 | GTCTCTGTGCTCTGCCTGTGCTG (SEQ ID NO. 143) |
| | lvf15 | GGTCTCTCTCCCAGCCTGTGCTG (SEQ ID NO. 144) |
| | lvf16 | GGTCTCTCTCCCAGCTTGTGCTG (SEQ ID NO. 145) |

TABLE 13 -continued

List of primers used in RT Library Construction

|  | | |
|---|---|---|
| | lvf17 | GTTCCCTCTCGCAGCCTGTGCT (SEQ ID NO. 146) |
| | lvf18 | GTTCCCTCTCGCAGGCTGTGCT (SEQ ID NO. 147) |
| | lvf19 | GGTCCAATTCTCAGACTGTGGTG AC (SEQ ID NO. 148) |
| | lvf20 | GGTCCAATTCCCAGGCTGTGGTG (SEQ ID NO. 149) |
| | lvf21 | GAGTGGATTCTCAGACTGTGGTG AC (SEQ ID NO. 150) |
| | lvf22 | GGTCCCTCTCCCAGCCTGTGC (SEQ ID NO. 151) |
| VL chain reverse primers | LCR | AGTGTGGCCTTGTTGGCTTG (SEQ ID NO. 152) |

The library sequencing and analysis are carried out according to the method described in embodiment 1, the correlation of high frequency CDR3 region between RACE library and RT library is compared, see FIGS. 6(a) and 6(b) for the analysis of CDR3 frequency correlation between RACE library and RT library.

The results show that the correlation $R^2$ value of heavy chain and Lambda chain CDR3 in the two libraries is about 0.7; as shown in FIG. 6(a), the consistency of the highest frequency heavy chain and light chain CDR3 is very good, the high frequency heavy chain and light chain CDR3 in the top 10 of antibody spectrum also show some consistency, indicating that there is no significant deviation in most of the high frequency CDR3 rankings in the two libraries. For example, the highest frequency CDR3 (ARETDGMDV) (SEQ ID NO.153) of heavy chain of the sample 11-2 in FIG. 6(b) is the highest frequency CDR3 in both RACE and RT libraries. The amino acid sequences of the most abundant FR and CDR regions of the CDR3-ARETDGMDV (SEQ ID NO.153) homology cluster selected by using the RACE R12 file are FR1:QVQLVQSGAEVKRPGASVKVSCKAS (SEQ ID NO.154), FR2:MHWVRQAPGQRLEWMGW (SEQ ID NO.155), FR3:KYSQKFQGRVTITRDTSAS-TAYMELSSLRSEDTAVYYC (SEQ ID NO.156), CDR1: GYTFTTYA (SEQ ID NO.157), FR4:WGQG (SEQ ID NO.50), CDR2:INAGNGNT (SEQ ID NO.158). The amino acid sequences of the most abundant FR region and CDR region of CDR3-ARETDGMDV (SEQ ID NO.153) homology cluster selected by RT file are also consistent, which indicates that this method can be used to splice the variable region of high frequency CDR3 gene.

Embodiment 5 an Optimized Antibody Gene Screening Method for HA Monoclonal Antibody Use the method of RACE antibody library construction described in embodiment 1, total RNAs are isolated from spleen cells of mice immunized with HA antigen, and construct the RACE libraries of heavy chain and light chain respectively. Use Illumina Miseq 2×250 system for high-throughput sequencing. The methods of data processing, the determination of FR and CDR regions, and the selection of candidate CDR3 amino acid sequences are the same as those described in embodiment 1.

The expression frame is constructed by fusion of PCR; the frame includes promoter, variable region and antibody constant region. The selected antibody heavy chain gene and light chain gene are randomly paired and transfected 293FT cells for expression and the supernatant is obtained for Elisa assay, its affinity to antigens is tested.

The concrete methods for expression in vitro can be referred to dengue virus cases. Elisa results show that one affinity antibody is obtained from the pairing of candidate heavy chain and light chain.

TABLE 14

Analysis of heavy chain CDR3 frequency after HA immunization in mice

| Heavy chain CDR3_Seq | Frequency after immunization (%) |
|---|---|
| TRGDY (SEQ ID NO. 159) | 5.94 |
| ARHTIPPYVMDY (SEQ ID NO. 160) | 1.56 |
| ARDEGIYGY (SEQ ID NO. 161) | 1.48 |
| ARGVYNYGRVWYFDV (SEQ ID NO. 162) | 1.36 |
| ARRDYDNYVPFAY (SEQ ID NO. 163) | 1.25 |
| TGDYEFGLFDY (SEQ ID NO. 164) | 1.24 |
| ARLSGTFAY (SEQ ID NO. 165) | 1.01 |
| ASLKGSAY (SEQ ID NO. 166) | 0.92 |
| AREGGYYFDY (SEQ ID NO. 167) | 0.91 |
| ARDNGHDWFAY (SEQ ID NO. 168) | 0.87 |
| ARRDYGNYVPFAY (SEQ ID NO. 169) | 0.76 |
| VLDYYGYAPFAY (SEQ ID NO. 170) | 0.75 |
| ARDLYYSHGGFAY (SEQ ID NO. 171) | 0.70 |
| ARVDGYLQGYYFGY (SEQ ID NO. 172) | 0.69 |
| ARGREGNGAMDY (SEQ ID NO. 173) | 0.65 |
| ARQEFYYGNYDAMDY (SEQ ID NO. 174) | 0.61 |
| ASGILNVMDY (SEQ ID NO. 175) | 0.58 |
| ARATVPAEIAY (SEQ ID NO. 176) | 0.57 |
| ARWTGTGDYAMDY (SEQ ID NO. 177) | 0.56 |
| ARSGLIYDGYYAWFAY (SEQ ID NO. 178) | 0.53 |

TABLE 15

Analysis of Kappa chain CDR3 frequency after HA immunization in mice

| Kappa chain | Frequency after immunization (%) |
|---|---|
| WQGTHFPWT (SEQ ID NO. 179) | 4.62 |
| QNGHSFPYT (SEQ ID NO. 180) | 4.11 |
| QQYYSYPRT (SEQ ID NO. 181) | 3.86 |
| QQYYRYPWT (SEQ ID NO. 182) | 1.97 |
| QQYYNYRT (SEQ ID NO. 183) | 1.92 |
| MQHLEYPFT (SEQ ID NO. 184) | 1.83 |
| QQYYSYPWT (SEQ ID NO. 185) | 1.49 |
| KQSYNLLT (SEQ ID NO. 186) | 1.31 |

TABLE 15 -continued

Analysis of Kappa chain CDR3 frequency after HA immunization in mice

| Kappa chain | Frequency after immunization (%) |
|---|---|
| LHYDNLWT (SEQ ID NO. 187) | 1.22 |
| QQYYSYRT (SEQ ID NO. 188) | 1.11 |
| LQYDNLLT (SEQ ID NO. 189) | 1.10 |
| MQHLEYPYT (SEQ ID NO. 190) | 1.04 |
| QNDHSFPLT (SEQ ID NO. 191) | 0.96 |
| SQSTHVPPT (SEQ ID NO. 192) | 0.89 |
| FQGSHVPWT (SEQ ID NO. 193) | 0.85 |
| WQGTHFPQT (SEQ ID NO. 194) | 0.84 |
| QQWSSNPFT (SEQ ID NO. 195) | 0.79 |
| QQWSSNPPT (SEQ ID NO. 196) | 0.79 |
| HQWSSYRT (SEQ ID NO. 197) | 0.78 |
| KQSYNLWT (SEQ ID NO. 198) | 0.76 |

The applicant declares that the detailed method of the invention is explained by the above embodiments, but the invention is not limited to the above detailed methods, that is, it does not mean that the invention should rely on the above detailed methods for implementation. Technicians in the technical field should understand that any improvement in the invention, the equivalent replacement of the raw materials of the products of the invention and the addition of auxiliary components, and the selection of concrete ways, etc., fall within the protection scope and the public scope of the invention.

The invention claimed is:

1. A method for identifying an influenza virus recombinant antibody comprising,
   (1) Extracting total RNA from at least one influenza virus immunized host, and constructing an antibody sequence library therefrom;
   (2) Performing high-throughput sequencing of variable regions of immunoglobulin genes present in said library thereby obtaining sequences of the antibody variable region genes for the target antigen;
   (3) Selecting a heavy chain CDR3 homologous cluster selected from the group consisting of SEQ ID NOS: 59, 60, 61, 62, 63, 64, 65, 66, 67, 68, 69, 70, 71, 72, 73, 74, 75, 76, 77, and 78, and selecting a light chain CDR3 homologous cluster selected from the group consisting of SEQ ID NOS: 79, 80, 81, 82, 83, 84, 85, 86, 87, 88, 89, 90, 91, 92, 93, 94, 95, 96, 97, and 98;
   (4) Identifying full length amino acid sequence of highest frequency antibody heavy chain variable region containing the heavy chain CDR3 homology cluster as a first candidate sequence, and identifying full length amino acid sequence of highest frequency antibody light chain variable region containing the light chain CDR3 homology cluster as a second candidate sequence;
   (5) Determining nucleic acid sequences of the first and second candidate sequences;
   (6) Expressing said nucleic acid sequences in vitro thereby producing a candidate influenza virus recombinant antibody comprising said CDR3 homologous clusters; and
   (7) Testing affinity to an antigen for the candidate influenza virus recombinant antibody, to determine if it is a functional antibody.

2. The method as claimed in claim 1, wherein said antibody sequence library is generated by RACE and/or RT library construction.

3. The method according to claim 2, where a RACE library is constructed and cDNA is synthesized by reverse transcription using oligo (dT) as primer and said isolated total RNA as template, said antibody sequence library being produced by using said synthesized cDNA as template.

4. The method according to claim 2, where an RT library is constructed and cDNA is synthesized by reverse transcription using oligo (dT) as primer and said isolated total RNA as template, said antibody sequence library being produced with specific primer separate amplification using said synthesized cDNA as template.

5. The method according to claim 1, wherein the host is selected from the group consisting of a mammal, an amphibian, a fish, a bird, and combinations thereof.

6. The method as claimed in claim 2, wherein the RACE library construction includes a PCR amplicon library construction method.

7. The method as claimed in claim 1, wherein the high-throughput sequencing is performed by one or more of sequencing by synthesis, sequencing by joining, sequencing by hybridization, single molecule DNA sequencing, multiple polymerase community sequencing or nano-pore sequencing.

8. The method of claim 5, wherein the mammal is selected from the group consisting of a human individual, a mouse, a primate, a rabbit, a goat, a sheep, and a pig.

9. The method of claim 8, wherein said total RNA is extracted from at least two of peripheral blood, lymphoid organs, spleen, bone marrow or liver.

10. The method of claim 1, wherein said total RNA is extracted from two or more cells selected from memory B cells, plasma cells, or plasmablasts.

11. The method of claim 6, wherein an antibody gene is amplified by a first round of PCR, and the amplification product is used for DNA library construction.

12. The method of claim 11, wherein the primers for PCR used in the first round of two-step PCR amplification include partial forward primer of SEQ ID NO: 1 and a partial reverse primer selected from SEQ ID NO. 2-4, wherein the partial forward joint sequence optionally includes 5-60 nucleotides of the 3' end of SEQ ID NO: 5, and the partial reverse joint sequence optionally includes 5-60 nucleotides of the 3' end of SEQ ID NO: 6.

13. The method of claim 11, wherein said forward joint primer is SEQ ID NO. 5, and the reverse joint primer is SEQ ID NO. 6.

14. The method as claimed in claim 2, wherein the RACE library construction includes a two-step PCR library construction method.

* * * * *

SEQUENCE LISTING

<160> NUMBER OF SEQ ID NOS: 201

<210> SEQ ID NO 1
<211> LENGTH: 24
<212> TYPE: DNA
<213> ORGANISM: Artificial Sequence
<220> FEATURE:
<223> OTHER INFORMATION: primer

<400> SEQUENCE: 1
aagcagtggt atcaacgcag agta                                          24

<210> SEQ ID NO 2
<211> LENGTH: 24
<212> TYPE: DNA
<213> ORGANISM: Artificial Sequence
<220> FEATURE:
<223> OTHER INFORMATION: primer

<400> SEQUENCE: 2
ggaagaccga tgggcccttg gtgg                                          24

<210> SEQ ID NO 3
<211> LENGTH: 27
<212> TYPE: DNA
<213> ORGANISM: Artificial Sequence
<220> FEATURE:
<223> OTHER INFORMATION: primer

<400> SEQUENCE: 3
gcaggcacac aacagaggca gttccag                                       27

<210> SEQ ID NO 4
<211> LENGTH: 25
<212> TYPE: DNA
<213> ORGANISM: Artificial Sequence
<220> FEATURE:
<223> OTHER INFORMATION: primer

<400> SEQUENCE: 4
cacaccagtg tggccttgtt ggctt                                         25

```
<210> SEQ ID NO 5
<211> LENGTH: 70
<212> TYPE: DNA
<213> ORGANISM: Artificial Sequence
<220> FEATURE:
<223> OTHER INFORMATION: primer

<400> SEQUENCE: 5
aatgatacgg cgaccaccga gatctacact atagcctaca ctctttccct acacgacgct      60
cttccgatct                                                            70

<210> SEQ ID NO 6
<211> LENGTH: 66
<212> TYPE: DNA
<213> ORGANISM: Artificial Sequence
<220> FEATURE:
<223> OTHER INFORMATION: primer

<400> SEQUENCE: 6
caagcagaag acggcatacg agatagcttc aggtgactgg agttcagacg tgtgctcttc      60
cgatct                                                                66

<210> SEQ ID NO 7
<211> LENGTH: 16
<212> TYPE: PRT
<213> ORGANISM: Artificial Sequence
<220> FEATURE:
<223> OTHER INFORMATION: Heavy chain CDR3 sequence

<400> SEQUENCE: 7

Ala Arg Ala Leu Ser Glu Lys Ser Leu Thr Thr Ser Tyr Leu Asp Cys
1               5                   10                  15

<210> SEQ ID NO 8
<211> LENGTH: 16
<212> TYPE: PRT
<213> ORGANISM: Artificial Sequence
<220> FEATURE:
<223> OTHER INFORMATION: Heavy chain CDR3 sequence

<400> SEQUENCE: 8

Val Lys Asp Ala Ser Thr Thr Ser Ile Gly Ala Ala Pro Phe Asp Tyr
1               5                   10                  15

<210> SEQ ID NO 9
<211> LENGTH: 12
<212> TYPE: PRT
<213> ORGANISM: Artificial Sequence
<220> FEATURE:
<223> OTHER INFORMATION: Heavy chain CDR3 sequence

<400> SEQUENCE: 9

Thr His Arg Arg Pro Ser Leu Arg Tyr Pro Asp Val
1               5                   10

<210> SEQ ID NO 10
<211> LENGTH: 13
<212> TYPE: PRT
<213> ORGANISM: Artificial Sequence
<220> FEATURE:
<223> OTHER INFORMATION: Heavy chain CDR3 sequence

<400> SEQUENCE: 10

Ala Ser Leu Gly Gly Thr Val Thr Asp Ala Phe Asp Leu
```

```
<210> SEQ ID NO 11
<211> LENGTH: 16
<212> TYPE: PRT
<213> ORGANISM: Artificial Sequence
<220> FEATURE:
<223> OTHER INFORMATION: Heavy chain CDR3 sequence

<400> SEQUENCE: 11

Ala Lys Asp Ala Ser Thr Thr Ser Lys Gly Ala Ala Pro Phe Asp Tyr
1               5                   10                  15

<210> SEQ ID NO 12
<211> LENGTH: 12
<212> TYPE: PRT
<213> ORGANISM: Artificial Sequence
<220> FEATURE:
<223> OTHER INFORMATION: Heavy chain CDR3 sequence

<400> SEQUENCE: 12

Ala Arg Gly Phe Thr Tyr Gly His Tyr Phe Asp Tyr
1               5                   10

<210> SEQ ID NO 13
<211> LENGTH: 16
<212> TYPE: PRT
<213> ORGANISM: Artificial Sequence
<220> FEATURE:
<223> OTHER INFORMATION: Heavy chain CDR3 sequence

<400> SEQUENCE: 13

Val Lys Asp Ala Ser Thr Thr Ser Ile Gly Ala Ala Pro Phe Asp Asn
1               5                   10                  15

<210> SEQ ID NO 14
<211> LENGTH: 13
<212> TYPE: PRT
<213> ORGANISM: Artificial Sequence
<220> FEATURE:
<223> OTHER INFORMATION: Heavy chain CDR3 sequence

<400> SEQUENCE: 14

Ala Lys Thr Val Val Thr Ala Pro Gly Val Phe Asp Tyr
1               5                   10

<210> SEQ ID NO 15
<211> LENGTH: 10
<212> TYPE: PRT
<213> ORGANISM: Artificial Sequence
<220> FEATURE:
<223> OTHER INFORMATION: Heavy chain CDR3 sequence

<400> SEQUENCE: 15

Ala Ser Asp Ile Leu Asp Ala Phe Asp Val
1               5                   10

<210> SEQ ID NO 16
<211> LENGTH: 16
<212> TYPE: PRT
<213> ORGANISM: Artificial Sequence
<220> FEATURE:
<223> OTHER INFORMATION: Heavy chain CDR3 sequence

<400> SEQUENCE: 16

Val Lys Asp Ala Ser Thr Thr Ser Ile Gly Ala Ala Pro Phe Asp Ser
1               5                   10                  15
```

<210> SEQ ID NO 17
<211> LENGTH: 13
<212> TYPE: PRT
<213> ORGANISM: Artificial Sequence
<220> FEATURE:
<223> OTHER INFORMATION: Heavy chain CDR3 sequence

<400> SEQUENCE: 17

Ala Ser Leu Gly Gly Thr Val Thr Asp Ala Phe Asp Val
1               5                   10

<210> SEQ ID NO 18
<211> LENGTH: 13
<212> TYPE: PRT
<213> ORGANISM: Artificial Sequence
<220> FEATURE:
<223> OTHER INFORMATION: Heavy chain CDR3 sequence

<400> SEQUENCE: 18

Ala Ser Leu Gly Gly Thr Val Thr Asp Ala Phe Asp Ile
1               5                   10

<210> SEQ ID NO 19
<211> LENGTH: 12
<212> TYPE: PRT
<213> ORGANISM: Artificial Sequence
<220> FEATURE:
<223> OTHER INFORMATION: Heavy chain CDR3 sequence

<400> SEQUENCE: 19

Ala Thr Gly Tyr Thr Tyr Gly Tyr Tyr Phe Asp Tyr
1               5                   10

<210> SEQ ID NO 20
<211> LENGTH: 9
<212> TYPE: PRT
<213> ORGANISM: Artificial Sequence
<220> FEATURE:
<223> OTHER INFORMATION: Kappa chain CDR3 sequence

<400> SEQUENCE: 20

Gln Gln Ala Asn Ser Phe Pro Trp Thr
1               5

<210> SEQ ID NO 21
<211> LENGTH: 11
<212> TYPE: PRT
<213> ORGANISM: Artificial Sequence
<220> FEATURE:
<223> OTHER INFORMATION: Kappa chain CDR3 sequence

<400> SEQUENCE: 21

His Gln Tyr Ser Ser Trp Pro Pro Gly Gly Thr
1               5                   10

<210> SEQ ID NO 22
<211> LENGTH: 11
<212> TYPE: PRT
<213> ORGANISM: Artificial Sequence
<220> FEATURE:
<223> OTHER INFORMATION: Kappa chain CDR3 sequence

<400> SEQUENCE: 22

His Gln Tyr Asn Ser Trp Pro Pro Gly Gly Thr
1               5                   10

<210> SEQ ID NO 23
<211> LENGTH: 11
<212> TYPE: PRT
<213> ORGANISM: Artificial Sequence
<220> FEATURE:
<223> OTHER INFORMATION: Kappa chain CDR3 sequence

<400> SEQUENCE: 23

His Gln Tyr Asn Ala Trp Pro Pro Gly Gly Thr
1               5                   10

<210> SEQ ID NO 24
<211> LENGTH: 8
<212> TYPE: PRT
<213> ORGANISM: Artificial Sequence
<220> FEATURE:
<223> OTHER INFORMATION: Kappa chain CDR3 sequence

<400> SEQUENCE: 24

Met Gln Gly Thr His Trp Arg Ser
1               5

<210> SEQ ID NO 25
<211> LENGTH: 9
<212> TYPE: PRT
<213> ORGANISM: Artificial Sequence
<220> FEATURE:
<223> OTHER INFORMATION: Kappa chain CDR3 sequence

<400> SEQUENCE: 25

Gln Gln Tyr Ser Phe Trp Pro Trp Thr
1               5

<210> SEQ ID NO 26
<211> LENGTH: 9
<212> TYPE: PRT
<213> ORGANISM: Artificial Sequence
<220> FEATURE:
<223> OTHER INFORMATION: Kappa chain CDR3 sequence

<400> SEQUENCE: 26

Gln Gln Tyr Asp Ser Phe Pro Leu Thr
1               5

<210> SEQ ID NO 27
<211> LENGTH: 9
<212> TYPE: PRT
<213> ORGANISM: Artificial Sequence
<220> FEATURE:
<223> OTHER INFORMATION: Kappa chain CDR3 sequence

<400> SEQUENCE: 27

Gln Gln Ala Asn Asn Phe Pro Trp Thr
1               5

<210> SEQ ID NO 28
<211> LENGTH: 11
<212> TYPE: PRT
<213> ORGANISM: Artificial Sequence
<220> FEATURE:
<223> OTHER INFORMATION: Kappa chain CDR3 sequence

<400> SEQUENCE: 28

His Gln Tyr Thr Ser Trp Pro Pro Gly Gly Thr
1               5                   10

```
<210> SEQ ID NO 29
<211> LENGTH: 9
<212> TYPE: PRT
<213> ORGANISM: Artificial Sequence
<220> FEATURE:
<223> OTHER INFORMATION: Kappa chain CDR3 sequence

<400> SEQUENCE: 29

Gln Gln Arg Ser Asn Trp Pro Arg Thr
1               5

<210> SEQ ID NO 30
<211> LENGTH: 9
<212> TYPE: PRT
<213> ORGANISM: Artificial Sequence
<220> FEATURE:
<223> OTHER INFORMATION: Kappa chain CDR3 sequence

<400> SEQUENCE: 30

Gln Gln Ile Ser Asn Phe Pro Ile Thr
1               5

<210> SEQ ID NO 31
<211> LENGTH: 9
<212> TYPE: PRT
<213> ORGANISM: Artificial Sequence
<220> FEATURE:
<223> OTHER INFORMATION: Kappa chain CDR3 sequence

<400> SEQUENCE: 31

Gln Gln Ser Phe Ser Pro Pro Trp Thr
1               5

<210> SEQ ID NO 32
<211> LENGTH: 9
<212> TYPE: PRT
<213> ORGANISM: Artificial Sequence
<220> FEATURE:
<223> OTHER INFORMATION: Kappa chain CDR3 sequence

<400> SEQUENCE: 32

Gln Gln Ser Gly Ser Ser Leu Ile Ile
1               5

<210> SEQ ID NO 33
<211> LENGTH: 9
<212> TYPE: PRT
<213> ORGANISM: Artificial Sequence
<220> FEATURE:
<223> OTHER INFORMATION: Kappa chain CDR3 sequence

<400> SEQUENCE: 33

Gln Gln Arg Ser Thr Trp Pro Tyr Thr
1               5

<210> SEQ ID NO 34
<211> LENGTH: 12
<212> TYPE: PRT
<213> ORGANISM: Artificial Sequence
<220> FEATURE:
<223> OTHER INFORMATION: Lambda chain CDR3 sequence

<400> SEQUENCE: 34

Cys Ser Tyr Ala Ala Ser Tyr Tyr Asp Thr Gly Val
1               5                   10

<210> SEQ ID NO 35
```

```
<211> LENGTH: 11
<212> TYPE: PRT
<213> ORGANISM: Artificial Sequence
<220> FEATURE:
<223> OTHER INFORMATION: Lambda chain CDR3 sequence

<400> SEQUENCE: 35

Ser Ser Tyr Arg Ser Ile Ser Pro Phe Tyr Val
1               5                   10

<210> SEQ ID NO 36
<211> LENGTH: 11
<212> TYPE: PRT
<213> ORGANISM: Artificial Sequence
<220> FEATURE:
<223> OTHER INFORMATION: Lambda chain CDR3 sequence

<400> SEQUENCE: 36

Ser Ser Tyr Arg Ser Ser Ser Pro Phe Tyr Val
1               5                   10

<210> SEQ ID NO 37
<211> LENGTH: 11
<212> TYPE: PRT
<213> ORGANISM: Artificial Sequence
<220> FEATURE:
<223> OTHER INFORMATION: Lambda chain CDR3 sequence

<400> SEQUENCE: 37

Gln Val Trp Asp Arg Ser Thr Asn His Arg Val
1               5                   10

<210> SEQ ID NO 38
<211> LENGTH: 11
<212> TYPE: PRT
<213> ORGANISM: Artificial Sequence
<220> FEATURE:
<223> OTHER INFORMATION: Lambda chain CDR3 sequence

<400> SEQUENCE: 38

Gln Val Trp Asp Arg Ser Ser Asp His Arg Leu
1               5                   10

<210> SEQ ID NO 39
<211> LENGTH: 11
<212> TYPE: PRT
<213> ORGANISM: Artificial Sequence
<220> FEATURE:
<223> OTHER INFORMATION: Lambda chain CDR3 sequence

<400> SEQUENCE: 39

Gln Ser Tyr Asp Thr Ser Leu Arg Ala Gly Val
1               5                   10

<210> SEQ ID NO 40
<211> LENGTH: 9
<212> TYPE: PRT
<213> ORGANISM: Artificial Sequence
<220> FEATURE:
<223> OTHER INFORMATION: Lambda chain CDR3 sequence

<400> SEQUENCE: 40

Ser Ser Tyr Thr Gly Ser Ser Thr Val
1               5

<210> SEQ ID NO 41
<211> LENGTH: 10
```

```
<212> TYPE: PRT
<213> ORGANISM: Artificial Sequence
<220> FEATURE:
<223> OTHER INFORMATION: Lambda chain CDR3 sequence

<400> SEQUENCE: 41

Leu Leu Ser Tyr Gly Gly Ala Pro Cys Val
1               5                   10

<210> SEQ ID NO 42
<211> LENGTH: 10
<212> TYPE: PRT
<213> ORGANISM: Artificial Sequence
<220> FEATURE:
<223> OTHER INFORMATION: Lambda chain CDR3 sequence

<400> SEQUENCE: 42

Cys Ser Tyr Ala Gly Arg Ser Thr Trp Val
1               5                   10

<210> SEQ ID NO 43
<211> LENGTH: 11
<212> TYPE: PRT
<213> ORGANISM: Artificial Sequence
<220> FEATURE:
<223> OTHER INFORMATION: Lambda chain CDR3 sequence

<400> SEQUENCE: 43

Gln Ser Phe Asp Asp Ser Leu Ser Gly Trp Val
1               5                   10

<210> SEQ ID NO 44
<211> LENGTH: 11
<212> TYPE: PRT
<213> ORGANISM: Artificial Sequence
<220> FEATURE:
<223> OTHER INFORMATION: Lambda chain CDR3 sequence

<400> SEQUENCE: 44

Gln Val Trp Asp Arg Ser Thr Asn His Arg Leu
1               5                   10

<210> SEQ ID NO 45
<211> LENGTH: 10
<212> TYPE: PRT
<213> ORGANISM: Artificial Sequence
<220> FEATURE:
<223> OTHER INFORMATION: Lambda chain CDR3 sequence

<400> SEQUENCE: 45

Cys Ser Tyr Ala Gly Ser Asn Thr Trp Ile
1               5                   10

<210> SEQ ID NO 46
<211> LENGTH: 10
<212> TYPE: PRT
<213> ORGANISM: Artificial Sequence
<220> FEATURE:
<223> OTHER INFORMATION: Lambda chain CDR3 sequence

<400> SEQUENCE: 46

Cys Ser Tyr Ala Gly Ser Asn Thr Trp Val
1               5                   10

<210> SEQ ID NO 47
<211> LENGTH: 10
<212> TYPE: PRT
```

<213> ORGANISM: Artificial Sequence
<220> FEATURE:
<223> OTHER INFORMATION: CDR1

<400> SEQUENCE: 47

Gly Phe Ser Leu Ser Thr Ser Gly Val Gly
1               5                   10

<210> SEQ ID NO 48
<211> LENGTH: 25
<212> TYPE: PRT
<213> ORGANISM: Artificial Sequence
<220> FEATURE:
<223> OTHER INFORMATION: FR1

<400> SEQUENCE: 48

Gln Ile Thr Leu Lys Glu Ser Gly Pro Met Leu Val Lys Pro Thr Gln
1               5                   10                  15

Thr Leu Thr Leu Thr Cys Thr Phe Ser
            20                  25

<210> SEQ ID NO 49
<211> LENGTH: 38
<212> TYPE: PRT
<213> ORGANISM: Artificial Sequence
<220> FEATURE:
<223> OTHER INFORMATION: FR3

<400> SEQUENCE: 49

Arg Tyr Ser Pro Ser Leu Arg Ser Arg Leu Thr Ile Ser Lys Asp Thr
1               5                   10                  15

Ser Lys Asn Gln Val Val Leu Thr Met Thr Asn Leu Asp Pro Val Asp
            20                  25                  30

Thr Ala Thr Tyr Phe Cys
        35

<210> SEQ ID NO 50
<211> LENGTH: 4
<212> TYPE: PRT
<213> ORGANISM: Artificial Sequence
<220> FEATURE:
<223> OTHER INFORMATION: FR4

<400> SEQUENCE: 50

Trp Gly Gln Gly
1

<210> SEQ ID NO 51
<211> LENGTH: 17
<212> TYPE: PRT
<213> ORGANISM: Artificial Sequence
<220> FEATURE:
<223> OTHER INFORMATION: FR2

<400> SEQUENCE: 51

Val Gly Trp Ile Arg Gln Pro Pro Gly Glu Ala Leu Glu Trp Leu Ala
1               5                   10                  15

Ile

<210> SEQ ID NO 52
<211> LENGTH: 7
<212> TYPE: PRT
<213> ORGANISM: Artificial Sequence
<220> FEATURE:
<223> OTHER INFORMATION: CDR2

```
<400> SEQUENCE: 52

Ile Tyr Trp Asp Asp Lys
1               5

<210> SEQ ID NO 53
<211> LENGTH: 6
<212> TYPE: PRT
<213> ORGANISM: Artificial Sequence
<220> FEATURE:
<223> OTHER INFORMATION: CDR1

<400> SEQUENCE: 53

Gln Ser Val Ser Ser Asn
1               5

<210> SEQ ID NO 54
<211> LENGTH: 26
<212> TYPE: PRT
<213> ORGANISM: Artificial Sequence
<220> FEATURE:
<223> OTHER INFORMATION: FR1

<400> SEQUENCE: 54

Glu Ile Val Met Thr Gln Ser Pro Ala Thr Leu Ser Val Ser Pro Gly
1               5                   10                  15

Glu Arg Ala Thr Leu Ser Cys Arg Ala Ser
            20                  25

<210> SEQ ID NO 55
<211> LENGTH: 36
<212> TYPE: PRT
<213> ORGANISM: Artificial Sequence
<220> FEATURE:
<223> OTHER INFORMATION: FR3

<400> SEQUENCE: 55

Thr Arg Ala Ala Gly Ile Pro Asp Arg Phe Ser Gly Ser Gly Ser Gly
1               5                   10                  15

Thr Glu Phe Thr Leu Thr Ile Ser Ser Leu Gln Ser Glu Asp Phe Ala
            20                  25                  30

Val Tyr Phe Cys
        35

<210> SEQ ID NO 56
<211> LENGTH: 5
<212> TYPE: PRT
<213> ORGANISM: Artificial Sequence
<220> FEATURE:
<223> OTHER INFORMATION: FR4

<400> SEQUENCE: 56

Phe Gly Gln Gly Thr
1               5

<210> SEQ ID NO 57
<211> LENGTH: 17
<212> TYPE: PRT
<213> ORGANISM: Artificial Sequence
<220> FEATURE:
<223> OTHER INFORMATION: FR2

<400> SEQUENCE: 57

Leu Ala Trp Tyr Gln His Lys Pro Gly Gln Ala Pro Arg Leu Leu Leu
1               5                   10                  15
```

Tyr

<210> SEQ ID NO 58
<211> LENGTH: 3
<212> TYPE: PRT
<213> ORGANISM: Artificial Sequence
<220> FEATURE:
<223> OTHER INFORMATION: CDR2

<400> SEQUENCE: 58

Gly Ala Ser
1

<210> SEQ ID NO 59
<211> LENGTH: 10
<212> TYPE: PRT
<213> ORGANISM: Artificial Sequence
<220> FEATURE:
<223> OTHER INFORMATION: Heavy chain CDR3 Seq

<400> SEQUENCE: 59

Met Ser Trp Asn Asp Arg Val Val Ala Pro
1               5                   10

<210> SEQ ID NO 60
<211> LENGTH: 8
<212> TYPE: PRT
<213> ORGANISM: Artificial Sequence
<220> FEATURE:
<223> OTHER INFORMATION: Heavy chain CDR3 Seq

<400> SEQUENCE: 60

Ser Val Val Ser Phe Pro Pro Tyr
1               5

<210> SEQ ID NO 61
<211> LENGTH: 8
<212> TYPE: PRT
<213> ORGANISM: Artificial Sequence
<220> FEATURE:
<223> OTHER INFORMATION: Heavy chain CDR3 Seq

<400> SEQUENCE: 61

Glu Val Gly Gly Glu Arg Ala Tyr
1               5

<210> SEQ ID NO 62
<211> LENGTH: 10
<212> TYPE: PRT
<213> ORGANISM: Artificial Sequence
<220> FEATURE:
<223> OTHER INFORMATION: Heavy chain CDR3 Seq

<400> SEQUENCE: 62

Asp Arg Asp Ala Ser Gly Asp Phe Asp Ile
1               5                   10

<210> SEQ ID NO 63
<211> LENGTH: 8
<212> TYPE: PRT
<213> ORGANISM: Artificial Sequence
<220> FEATURE:
<223> OTHER INFORMATION: Heavy chain CDR3 Seq

<400> SEQUENCE: 63

Ala Pro Gly Gly Gln Trp Ala Tyr

```
1               5
```

<210> SEQ ID NO 64
<211> LENGTH: 9
<212> TYPE: PRT
<213> ORGANISM: Artificial Sequence
<220> FEATURE:
<223> OTHER INFORMATION: Heavy chain CDR3 Seq

<400> SEQUENCE: 64

```
Ser Ser Val Val Ser Phe Pro Pro Tyr
1               5
```

<210> SEQ ID NO 65
<211> LENGTH: 14
<212> TYPE: PRT
<213> ORGANISM: Artificial Sequence
<220> FEATURE:
<223> OTHER INFORMATION: Heavy chain CDR3 Seq

<400> SEQUENCE: 65

```
Asp Arg Val Thr Gly Asp Asn Phe Tyr Tyr Tyr Met Gly Val
1               5                   10
```

<210> SEQ ID NO 66
<211> LENGTH: 8
<212> TYPE: PRT
<213> ORGANISM: Artificial Sequence
<220> FEATURE:
<223> OTHER INFORMATION: Heavy chain CDR3 Seq

<400> SEQUENCE: 66

```
Gly Ser Thr Ile Met Val Thr Leu
1               5
```

<210> SEQ ID NO 67
<211> LENGTH: 11
<212> TYPE: PRT
<213> ORGANISM: Artificial Sequence
<220> FEATURE:
<223> OTHER INFORMATION: Heavy chain CDR3 Seq

<400> SEQUENCE: 67

```
Leu Gln Phe Phe Glu Gly Arg His Met Asp Val
1               5                   10
```

<210> SEQ ID NO 68
<211> LENGTH: 10
<212> TYPE: PRT
<213> ORGANISM: Artificial Sequence
<220> FEATURE:
<223> OTHER INFORMATION: Heavy chain CDR3 Seq

<400> SEQUENCE: 68

```
Asp Arg Val Ala Ser Gly Asp Phe Asp Ile
1               5                   10
```

<210> SEQ ID NO 69
<211> LENGTH: 16
<212> TYPE: PRT
<213> ORGANISM: Artificial Sequence
<220> FEATURE:
<223> OTHER INFORMATION: Heavy chain CDR3 Seq

<400> SEQUENCE: 69

```
Leu Leu Ser Gly Gly Glu Asn Pro Ser Tyr Tyr Tyr His Met Asp Val
1               5                   10                  15
```

<210> SEQ ID NO 70
<211> LENGTH: 13
<212> TYPE: PRT
<213> ORGANISM: Artificial Sequence
<220> FEATURE:
<223> OTHER INFORMATION: Heavy chain CDR3 Seq

<400> SEQUENCE: 70

Lys Thr Tyr Gly Ser Gly Ser Phe Asp Tyr Phe Asp Tyr
1               5                   10

<210> SEQ ID NO 71
<211> LENGTH: 10
<212> TYPE: PRT
<213> ORGANISM: Artificial Sequence
<220> FEATURE:
<223> OTHER INFORMATION: Heavy chain CDR3 Seq

<400> SEQUENCE: 71

Gly Ala Thr Val Val Asn Asp Leu Glu Tyr
1               5                   10

<210> SEQ ID NO 72
<211> LENGTH: 8
<212> TYPE: PRT
<213> ORGANISM: Artificial Sequence
<220> FEATURE:
<223> OTHER INFORMATION: Heavy chain CDR3 Seq

<400> SEQUENCE: 72

Gly Gly Thr Ile Arg Val Thr Leu
1               5

<210> SEQ ID NO 73
<211> LENGTH: 10
<212> TYPE: PRT
<213> ORGANISM: Artificial Sequence
<220> FEATURE:
<223> OTHER INFORMATION: Heavy chain CDR3 Seq

<400> SEQUENCE: 73

Met Asn Trp Asn Asp Arg Val Val Asp Pro
1               5                   10

<210> SEQ ID NO 74
<211> LENGTH: 8
<212> TYPE: PRT
<213> ORGANISM: Artificial Sequence
<220> FEATURE:
<223> OTHER INFORMATION: Heavy chain CDR3 Seq

<400> SEQUENCE: 74

Gly Gly Thr Ile Met Val Thr Leu
1               5

<210> SEQ ID NO 75
<211> LENGTH: 12
<212> TYPE: PRT
<213> ORGANISM: Artificial Sequence
<220> FEATURE:
<223> OTHER INFORMATION: Heavy chain CDR3 Seq

<400> SEQUENCE: 75

Asp Tyr Leu Ser Gly Thr Tyr Thr Pro Pro Leu Tyr
1               5                   10

<210> SEQ ID NO 76
<211> LENGTH: 18
<212> TYPE: PRT
<213> ORGANISM: Artificial Sequence
<220> FEATURE:
<223> OTHER INFORMATION: Heavy chain CDR3 Seq

<400> SEQUENCE: 76

Glu Arg Gly Glu Val Gly Asp Ser Val Asp Asn Phe Tyr Tyr Tyr Met
1               5                   10                  15

Asp Val

<210> SEQ ID NO 77
<211> LENGTH: 18
<212> TYPE: PRT
<213> ORGANISM: Artificial Sequence
<220> FEATURE:
<223> OTHER INFORMATION: Heavy chain CDR3 Seq

<400> SEQUENCE: 77

Pro Met Thr Tyr Tyr Tyr Asp Ile Ser Asp Ala Gly Ala Tyr Tyr Phe
1               5                   10                  15

Asp Thr

<210> SEQ ID NO 78
<211> LENGTH: 12
<212> TYPE: PRT
<213> ORGANISM: Artificial Sequence
<220> FEATURE:
<223> OTHER INFORMATION: Heavy chain CDR3 Seq

<400> SEQUENCE: 78

Pro Pro Thr Ala His His Phe Asn Ala Phe Tyr Ile
1               5                   10

<210> SEQ ID NO 79
<211> LENGTH: 9
<212> TYPE: PRT
<213> ORGANISM: Artificial Sequence
<220> FEATURE:
<223> OTHER INFORMATION: Kappa chain CDR3 Seq

<400> SEQUENCE: 79

Gln Gln Arg Ser Asp Trp Pro Tyr Thr
1               5

<210> SEQ ID NO 80
<211> LENGTH: 5
<212> TYPE: PRT
<213> ORGANISM: Artificial Sequence
<220> FEATURE:
<223> OTHER INFORMATION: Kappa chain CDR3 Seq

<400> SEQUENCE: 80

Gln Gln Tyr Asp Ala
1               5

<210> SEQ ID NO 81
<211> LENGTH: 9
<212> TYPE: PRT
<213> ORGANISM: Artificial Sequence
<220> FEATURE:
<223> OTHER INFORMATION: Kappa chain CDR3 Seq

<400> SEQUENCE: 81

His Gln Ser Ser Ile Arg Ser Trp Thr
1               5

<210> SEQ ID NO 82
<211> LENGTH: 9
<212> TYPE: PRT
<213> ORGANISM: Artificial Sequence
<220> FEATURE:
<223> OTHER INFORMATION: Kappa chain CDR3 Seq

<400> SEQUENCE: 82

Leu Gln His Asn Thr Tyr Pro Gln Thr
1               5

<210> SEQ ID NO 83
<211> LENGTH: 9
<212> TYPE: PRT
<213> ORGANISM: Artificial Sequence
<220> FEATURE:
<223> OTHER INFORMATION: Kappa chain CDR3 Seq

<400> SEQUENCE: 83

Gln Gln Ser Ser Thr Ser Ser Trp Thr
1               5

<210> SEQ ID NO 84
<211> LENGTH: 10
<212> TYPE: PRT
<213> ORGANISM: Artificial Sequence
<220> FEATURE:
<223> OTHER INFORMATION: Kappa chain CDR3 Seq

<400> SEQUENCE: 84

Gln Gln Tyr Asn Asn Trp Pro Pro Tyr Thr
1               5                   10

<210> SEQ ID NO 85
<211> LENGTH: 8
<212> TYPE: PRT
<213> ORGANISM: Artificial Sequence
<220> FEATURE:
<223> OTHER INFORMATION: Kappa chain CDR3 Seq

<400> SEQUENCE: 85

Met Gln Gly Lys Tyr Trp Pro Thr
1               5

<210> SEQ ID NO 86
<211> LENGTH: 9
<212> TYPE: PRT
<213> ORGANISM: Artificial Sequence
<220> FEATURE:
<223> OTHER INFORMATION: Kappa chain CDR3 Seq

<400> SEQUENCE: 86

Gln Gln Tyr Arg Gly Ser Ser Cys Thr
1               5

<210> SEQ ID NO 87
<211> LENGTH: 10
<212> TYPE: PRT
<213> ORGANISM: Artificial Sequence
<220> FEATURE:
<223> OTHER INFORMATION: Kappa chain CDR3 Seq

<400> SEQUENCE: 87

Gln Gln Tyr Gly Ser Ser Pro Pro Trp Thr

<210> SEQ ID NO 88
<211> LENGTH: 9
<212> TYPE: PRT
<213> ORGANISM: Artificial Sequence
<220> FEATURE:
<223> OTHER INFORMATION: Kappa chain CDR3 Seq

<400> SEQUENCE: 88

Gln Gln Tyr Asp Tyr Ser Ser Ser Thr
1               5

<210> SEQ ID NO 89
<211> LENGTH: 11
<212> TYPE: PRT
<213> ORGANISM: Artificial Sequence
<220> FEATURE:
<223> OTHER INFORMATION: Lambda chain-CDR3 Seq

<400> SEQUENCE: 89

Ala Ala Trp Asp Asp Asp Leu Ser Gly Pro Val
1               5                   10

<210> SEQ ID NO 90
<211> LENGTH: 11
<212> TYPE: PRT
<213> ORGANISM: Artificial Sequence
<220> FEATURE:
<223> OTHER INFORMATION: Lambda chain-CDR3 Seq

<400> SEQUENCE: 90

Ala Ala Trp Asp Asp Ser Gln Asn Gly Pro Leu
1               5                   10

<210> SEQ ID NO 91
<211> LENGTH: 2
<212> TYPE: PRT
<213> ORGANISM: Artificial Sequence
<220> FEATURE:
<223> OTHER INFORMATION: Lambda chain-CDR3 Seq

<400> SEQUENCE: 91

Gln Thr
1

<210> SEQ ID NO 92
<211> LENGTH: 11
<212> TYPE: PRT
<213> ORGANISM: Artificial Sequence
<220> FEATURE:
<223> OTHER INFORMATION: Lambda chain-CDR3 Seq

<400> SEQUENCE: 92

Ala Thr Trp Asp Asp Asn Leu Ser Gly Pro Val
1               5                   10

<210> SEQ ID NO 93
<211> LENGTH: 2
<212> TYPE: PRT
<213> ORGANISM: Artificial Sequence
<220> FEATURE:
<223> OTHER INFORMATION: Lambda chain-CDR3 Seq

<400> SEQUENCE: 93

Gln Val
1

```
<210> SEQ ID NO 94
<211> LENGTH: 12
<212> TYPE: PRT
<213> ORGANISM: Artificial Sequence
<220> FEATURE:
<223> OTHER INFORMATION: Lambda chain-CDR3 Seq

<400> SEQUENCE: 94

Ala Ala Trp Asp Asp Asn Phe Ser Gly Ala Glu Val
1               5                   10

<210> SEQ ID NO 95
<211> LENGTH: 11
<212> TYPE: PRT
<213> ORGANISM: Artificial Sequence
<220> FEATURE:
<223> OTHER INFORMATION: Lambda chain-CDR3 Seq

<400> SEQUENCE: 95

Ser Ser Tyr Thr Ser Ser Ser Thr Pro Trp Val
1               5                   10

<210> SEQ ID NO 96
<211> LENGTH: 12
<212> TYPE: PRT
<213> ORGANISM: Artificial Sequence
<220> FEATURE:
<223> OTHER INFORMATION: Lambda chain-CDR3 Seq

<400> SEQUENCE: 96

Ala Val Trp Asp Asn Ser Leu Asn Gly Phe Tyr Val
1               5                   10

<210> SEQ ID NO 97
<211> LENGTH: 12
<212> TYPE: PRT
<213> ORGANISM: Artificial Sequence
<220> FEATURE:
<223> OTHER INFORMATION: Lambda chain-CDR3 Seq

<400> SEQUENCE: 97

Ala Ala Trp Asp Asp Ser Leu Ser Pro Pro Glu Val
1               5                   10

<210> SEQ ID NO 98
<211> LENGTH: 11
<212> TYPE: PRT
<213> ORGANISM: Artificial Sequence
<220> FEATURE:
<223> OTHER INFORMATION: Lambda chain-CDR3 Seq

<400> SEQUENCE: 98

Ala Thr Trp Asp Asp Asp Leu Ser Gly Pro Val
1               5                   10

<210> SEQ ID NO 99
<211> LENGTH: 19
<212> TYPE: DNA
<213> ORGANISM: Artificial Sequence
<220> FEATURE:
<223> OTHER INFORMATION: IGHV_LR1 primer

<400> SEQUENCE: 99
cgcagaccct ctcactcac                                           19
```

```
<210> SEQ ID NO 100
<211> LENGTH: 20
<212> TYPE: DNA
<213> ORGANISM: Artificial Sequence
<220> FEATURE:
<223> OTHER INFORMATION: IGHV_LR2 primer

<400> SEQUENCE: 100
tggagctgag gtgaagaagc                                           20

<210> SEQ ID NO 101
<211> LENGTH: 20
<212> TYPE: DNA
<213> ORGANISM: Artificial Sequence
<220> FEATURE:
<223> OTHER INFORMATION: IGHV_LR3 primer

<400> SEQUENCE: 101
tgcaatctgg gtctgagttg                                           20

<210> SEQ ID NO 102
<211> LENGTH: 19
<212> TYPE: DNA
<213> ORGANISM: Artificial Sequence
<220> FEATURE:
<223> OTHER INFORMATION: IGHV_LR4 primer

<400> SEQUENCE: 102
ggctcaggac tggtgaagc                                            19

<210> SEQ ID NO 103
<211> LENGTH: 20
<212> TYPE: DNA
<213> ORGANISM: Artificial Sequence
<220> FEATURE:
<223> OTHER INFORMATION: IGHV_LR5 primer

<400> SEQUENCE: 103
tggagcagag gtgaaaaagc                                           20

<210> SEQ ID NO 104
<211> LENGTH: 19
<212> TYPE: DNA
<213> ORGANISM: Artificial Sequence
<220> FEATURE:
<223> OTHER INFORMATION: IGHV_LR6 primer

<400> SEQUENCE: 104
ggtgcagctg ttggagtct                                            19

<210> SEQ ID NO 105
<211> LENGTH: 20
<212> TYPE: DNA
<213> ORGANISM: Artificial Sequence
<220> FEATURE:
<223> OTHER INFORMATION: IGHV_LR7 primer

<400> SEQUENCE: 105
actgttgaag ccttcggaga                                           20

<210> SEQ ID NO 106
<211> LENGTH: 20
<212> TYPE: DNA
<213> ORGANISM: Artificial Sequence
<220> FEATURE:
<223> OTHER INFORMATION: IGHV_LR8 primer
```

<400> SEQUENCE: 106
aaacccacac agaccctcac                                           20

<210> SEQ ID NO 107
<211> LENGTH: 20
<212> TYPE: DNA
<213> ORGANISM: Artificial Sequence
<220> FEATURE:
<223> OTHER INFORMATION: IGHV_LR9 primer

<400> SEQUENCE: 107
agtctggggc tgaggtgaag                                           20

<210> SEQ ID NO 108
<211> LENGTH: 18
<212> TYPE: DNA
<213> ORGANISM: Artificial Sequence
<220> FEATURE:
<223> OTHER INFORMATION: IGHV_LR10 primer

<400> SEQUENCE: 108
ggcccaggac tggtgaag                                             18

<210> SEQ ID NO 109
<211> LENGTH: 18
<212> TYPE: DNA
<213> ORGANISM: Artificial Sequence
<220> FEATURE:
<223> OTHER INFORMATION: IGHV_LR11 primer

<400> SEQUENCE: 109
ggtgcagctg gtggagtc                                             18

<210> SEQ ID NO 110
<211> LENGTH: 18
<212> TYPE: DNA
<213> ORGANISM: Artificial Sequence
<220> FEATURE:
<223> OTHER INFORMATION: HGR primer

<400> SEQUENCE: 110
aagaccgatg ggcccttg                                             18

<210> SEQ ID NO 111
<211> LENGTH: 20
<212> TYPE: DNA
<213> ORGANISM: Artificial Sequence
<220> FEATURE:
<223> OTHER INFORMATION: kvf1 primer

<400> SEQUENCE: 111
tgacccagtc tccatcctcc                                           20

<210> SEQ ID NO 112
<211> LENGTH: 20
<212> TYPE: DNA
<213> ORGANISM: Artificial Sequence
<220> FEATURE:
<223> OTHER INFORMATION: kvf2 primer

<400> SEQUENCE: 112
tgacccagtc tccatcctca                                           20

<210> SEQ ID NO 113
<211> LENGTH: 21

```
<212> TYPE: DNA
<213> ORGANISM: Artificial Sequence
<220> FEATURE:
<223> OTHER INFORMATION: kvf3 primer

<400> SEQUENCE: 113
tgacccagtc tccatccttc c                                              21

<210> SEQ ID NO 114
<211> LENGTH: 22
<212> TYPE: DNA
<213> ORGANISM: Artificial Sequence
<220> FEATURE:
<223> OTHER INFORMATION: kvf4 primer

<400> SEQUENCE: 114
tgacccagtc tccatcctta ct                                             22

<210> SEQ ID NO 115
<211> LENGTH: 20
<212> TYPE: DNA
<213> ORGANISM: Artificial Sequence
<220> FEATURE:
<223> OTHER INFORMATION: kvf5 primer

<400> SEQUENCE: 115
tgacccagtc tccatctgcc                                                20

<210> SEQ ID NO 116
<211> LENGTH: 20
<212> TYPE: DNA
<213> ORGANISM: Artificial Sequence
<220> FEATURE:
<223> OTHER INFORMATION: kvf6 primer

<400> SEQUENCE: 116
tgacccagtc tccatcttcc                                                20

<210> SEQ ID NO 117
<211> LENGTH: 20
<212> TYPE: DNA
<213> ORGANISM: Artificial Sequence
<220> FEATURE:
<223> OTHER INFORMATION: kvf7 primer

<400> SEQUENCE: 117
tgacacagtc tccagccacc                                                20

<210> SEQ ID NO 118
<211> LENGTH: 20
<212> TYPE: DNA
<213> ORGANISM: Artificial Sequence
<220> FEATURE:
<223> OTHER INFORMATION: kvf8 primer

<400> SEQUENCE: 118
tgacacagtc tccaggcacc                                                20

<210> SEQ ID NO 119
<211> LENGTH: 19
<212> TYPE: DNA
<213> ORGANISM: Artificial Sequence
<220> FEATURE:
<223> OTHER INFORMATION: kvf9 primer

<400> SEQUENCE: 119
```

```
tgacgcagtc tccaggcac                                                    19

<210> SEQ ID NO 120
<211> LENGTH: 20
<212> TYPE: DNA
<213> ORGANISM: Artificial Sequence
<220> FEATURE:
<223> OTHER INFORMATION: kvf10 primer

<400> SEQUENCE: 120
tgacccagtc tccagactcc                                                   20

<210> SEQ ID NO 121
<211> LENGTH: 21
<212> TYPE: DNA
<213> ORGANISM: Artificial Sequence
<220> FEATURE:
<223> OTHER INFORMATION: kvf11 primer

<400> SEQUENCE: 121
tgactcagtc tccactctcc c                                                 21

<210> SEQ ID NO 122
<211> LENGTH: 21
<212> TYPE: DNA
<213> ORGANISM: Artificial Sequence
<220> FEATURE:
<223> OTHER INFORMATION: kvf12 primer

<400> SEQUENCE: 122
tgacccagtc tccattctcc c                                                 21

<210> SEQ ID NO 123
<211> LENGTH: 21
<212> TYPE: DNA
<213> ORGANISM: Artificial Sequence
<220> FEATURE:
<223> OTHER INFORMATION: kvf13 primer

<400> SEQUENCE: 123
tgacccagac tccactctct c                                                 21

<210> SEQ ID NO 124
<211> LENGTH: 20
<212> TYPE: DNA
<213> ORGANISM: Artificial Sequence
<220> FEATURE:
<223> OTHER INFORMATION: kvf14 primer

<400> SEQUENCE: 124
tgacccagac tccactctcc                                                   20

<210> SEQ ID NO 125
<211> LENGTH: 20
<212> TYPE: DNA
<213> ORGANISM: Artificial Sequence
<220> FEATURE:
<223> OTHER INFORMATION: kvf15 primer

<400> SEQUENCE: 125
tgacccagtc tccttccacc                                                   20

<210> SEQ ID NO 126
<211> LENGTH: 20
<212> TYPE: DNA
<213> ORGANISM: Artificial Sequence
```

<220> FEATURE:
<223> OTHER INFORMATION: kvf16 primer

<400> SEQUENCE: 126
tcacgcagtc tccagcattc                                              20

<210> SEQ ID NO 127
<211> LENGTH: 19
<212> TYPE: DNA
<213> ORGANISM: Artificial Sequence
<220> FEATURE:
<223> OTHER INFORMATION: kvf17 primer

<400> SEQUENCE: 127
tgacgcagtc tccagccac                                               19

<210> SEQ ID NO 128
<211> LENGTH: 21
<212> TYPE: DNA
<213> ORGANISM: Artificial Sequence
<220> FEATURE:
<223> OTHER INFORMATION: kvf18 primer

<400> SEQUENCE: 128
tgacccagtc tccatcttct g                                            21

<210> SEQ ID NO 129
<211> LENGTH: 21
<212> TYPE: DNA
<213> ORGANISM: Artificial Sequence
<220> FEATURE:
<223> OTHER INFORMATION: KCR primer

<400> SEQUENCE: 129
acacaacaga ggcagttcca g                                            21

<210> SEQ ID NO 130
<211> LENGTH: 21
<212> TYPE: DNA
<213> ORGANISM: Artificial Sequence
<220> FEATURE:
<223> OTHER INFORMATION: lvf1 primer

<400> SEQUENCE: 130
ggtcctgggc ccagtctgtc g                                            21

<210> SEQ ID NO 131
<211> LENGTH: 20
<212> TYPE: DNA
<213> ORGANISM: Artificial Sequence
<220> FEATURE:
<223> OTHER INFORMATION: lvf2 primer

<400> SEQUENCE: 131
ggtcctgggc ccagtctgcc                                              20

<210> SEQ ID NO 132
<211> LENGTH: 21
<212> TYPE: DNA
<213> ORGANISM: Artificial Sequence
<220> FEATURE:
<223> OTHER INFORMATION: lvf3 primer

<400> SEQUENCE: 132
gtcctgggcc cagtctgtgc t                                            21

<210> SEQ ID NO 133
<211> LENGTH: 21
<212> TYPE: DNA
<213> ORGANISM: Artificial Sequence
<220> FEATURE:
<223> OTHER INFORMATION: lvf4 primer

<400> SEQUENCE: 133
tgtcagtggt ccaggcaggg c                                              21

<210> SEQ ID NO 134
<211> LENGTH: 23
<212> TYPE: DNA
<213> ORGANISM: Artificial Sequence
<220> FEATURE:
<223> OTHER INFORMATION: lvf5 primer

<400> SEQUENCE: 134
gatcctgggc tcagtctgcc ctg                                            23

<210> SEQ ID NO 135
<211> LENGTH: 23
<212> TYPE: DNA
<213> ORGANISM: Artificial Sequence
<220> FEATURE:
<223> OTHER INFORMATION: lvf6 primer

<400> SEQUENCE: 135
gctctgaggc ctcctatgag ctg                                            23

<210> SEQ ID NO 136
<211> LENGTH: 23
<212> TYPE: DNA
<213> ORGANISM: Artificial Sequence
<220> FEATURE:
<223> OTHER INFORMATION: lvf7 primer

<400> SEQUENCE: 136
gatccgtggc ctcctatgag ctg                                            23

<210> SEQ ID NO 137
<211> LENGTH: 23
<212> TYPE: DNA
<213> ORGANISM: Artificial Sequence
<220> FEATURE:
<223> OTHER INFORMATION: lvf8 primer

<400> SEQUENCE: 137
tctctgaggc ctcctatgag ctg                                            23

<210> SEQ ID NO 138
<211> LENGTH: 23
<212> TYPE: DNA
<213> ORGANISM: Artificial Sequence
<220> FEATURE:
<223> OTHER INFORMATION: lvf9 primer

<400> SEQUENCE: 138
gctctgcgac ctcctatgag ctg                                            23

<210> SEQ ID NO 139
<211> LENGTH: 25
<212> TYPE: DNA
<213> ORGANISM: Artificial Sequence
<220> FEATURE:
<223> OTHER INFORMATION: lvf10 primer

```
-continued

<400> SEQUENCE: 139
gttctgtggt ttcttctgag ctgac                                          25

<210> SEQ ID NO 140
<211> LENGTH: 23
<212> TYPE: DNA
<213> ORGANISM: Artificial Sequence
<220> FEATURE:
<223> OTHER INFORMATION: lvf11 primer

<400> SEQUENCE: 140
gctctgtgac ctcctatgtg ctg                                            23

<210> SEQ ID NO 141
<211> LENGTH: 23
<212> TYPE: DNA
<213> ORGANISM: Artificial Sequence
<220> FEATURE:
<223> OTHER INFORMATION: lvf12 primer

<400> SEQUENCE: 141
tctctgtggc ctcctatgag ctg                                            23

<210> SEQ ID NO 142
<211> LENGTH: 23
<212> TYPE: DNA
<213> ORGANISM: Artificial Sequence
<220> FEATURE:
<223> OTHER INFORMATION: lvf13 primer

<400> SEQUENCE: 142
gttctgtggc ctcctatgag ctg                                            23

<210> SEQ ID NO 143
<211> LENGTH: 23
<212> TYPE: DNA
<213> ORGANISM: Artificial Sequence
<220> FEATURE:
<223> OTHER INFORMATION: lvf14 primer

<400> SEQUENCE: 143
gtctctgtgc tctgcctgtg ctg                                            23

<210> SEQ ID NO 144
<211> LENGTH: 23
<212> TYPE: DNA
<213> ORGANISM: Artificial Sequence
<220> FEATURE:
<223> OTHER INFORMATION: lvf15 primer

<400> SEQUENCE: 144
ggtctctctc ccagcctgtg ctg                                            23

<210> SEQ ID NO 145
<211> LENGTH: 23
<212> TYPE: DNA
<213> ORGANISM: Artificial Sequence
<220> FEATURE:
<223> OTHER INFORMATION: lvf16 primer

<400> SEQUENCE: 145
ggtctctctc ccagcttgtg ctg                                            23

<210> SEQ ID NO 146
```

```
<211> LENGTH: 22
<212> TYPE: DNA
<213> ORGANISM: Artificial Sequence
<220> FEATURE:
<223> OTHER INFORMATION: lvf17 primer

<400> SEQUENCE: 146
gttccctctc gcagcctgtg ct                                              22

<210> SEQ ID NO 147
<211> LENGTH: 22
<212> TYPE: DNA
<213> ORGANISM: Artificial Sequence
<220> FEATURE:
<223> OTHER INFORMATION: lvf18 primer

<400> SEQUENCE: 147
gttccctctc gcaggctgtg ct                                              22

<210> SEQ ID NO 148
<211> LENGTH: 25
<212> TYPE: DNA
<213> ORGANISM: Artificial Sequence
<220> FEATURE:
<223> OTHER INFORMATION: lvf19 primer

<400> SEQUENCE: 148
ggtccaattc tcagactgtg gtgac                                           25

<210> SEQ ID NO 149
<211> LENGTH: 23
<212> TYPE: DNA
<213> ORGANISM: Artificial Sequence
<220> FEATURE:
<223> OTHER INFORMATION: lvf20 primer

<400> SEQUENCE: 149
ggtccaattc ccaggctgtg gtg                                             23

<210> SEQ ID NO 150
<211> LENGTH: 25
<212> TYPE: DNA
<213> ORGANISM: Artificial Sequence
<220> FEATURE:
<223> OTHER INFORMATION: lvf21 primer

<400> SEQUENCE: 150
gagtggattc tcagactgtg gtgac                                           25

<210> SEQ ID NO 151
<211> LENGTH: 21
<212> TYPE: DNA
<213> ORGANISM: Artificial Sequence
<220> FEATURE:
<223> OTHER INFORMATION: lvf22 primer

<400> SEQUENCE: 151
ggtccctctc ccagcctgtg c                                               21

<210> SEQ ID NO 152
<211> LENGTH: 20
<212> TYPE: DNA
<213> ORGANISM: Artificial Sequence
<220> FEATURE:
<223> OTHER INFORMATION: LCR primer

<400> SEQUENCE: 152
```
agtgtggcct tgttggcttg                                           20

<210> SEQ ID NO 153
<211> LENGTH: 9
<212> TYPE: PRT
<213> ORGANISM: Artificial Sequence
<220> FEATURE:
<223> OTHER INFORMATION: CDR3

<400> SEQUENCE: 153

Ala Arg Glu Thr Asp Gly Met Asp Val
1               5

<210> SEQ ID NO 154
<211> LENGTH: 25
<212> TYPE: PRT
<213> ORGANISM: Artificial Sequence
<220> FEATURE:
<223> OTHER INFORMATION: FR1

<400> SEQUENCE: 154

Gln Val Gln Leu Val Gln Ser Gly Ala Glu Val Lys Arg Pro Gly Ala
1               5                   10                  15

Ser Val Lys Val Ser Cys Lys Ala Ser
            20                  25

<210> SEQ ID NO 155
<211> LENGTH: 17
<212> TYPE: PRT
<213> ORGANISM: Artificial Sequence
<220> FEATURE:
<223> OTHER INFORMATION: FR2

<400> SEQUENCE: 155

Met His Trp Val Arg Gln Ala Pro Gly Gln Arg Leu Glu Trp Met Gly
1               5                   10                  15

Trp

<210> SEQ ID NO 156
<211> LENGTH: 38
<212> TYPE: PRT
<213> ORGANISM: Artificial Sequence
<220> FEATURE:
<223> OTHER INFORMATION: FR3

<400> SEQUENCE: 156

Lys Tyr Ser Gln Lys Phe Gln Gly Arg Val Thr Ile Thr Arg Asp Thr
1               5                   10                  15

Ser Ala Ser Thr Ala Tyr Met Glu Leu Ser Ser Leu Arg Ser Glu Asp
            20                  25                  30

Thr Ala Val Tyr Tyr Cys
        35

<210> SEQ ID NO 157
<211> LENGTH: 8
<212> TYPE: PRT
<213> ORGANISM: Artificial Sequence
<220> FEATURE:
<223> OTHER INFORMATION: CDR1

<400> SEQUENCE: 157

Gly Tyr Thr Phe Thr Thr Tyr Ala
1               5

<210> SEQ ID NO 158
<211> LENGTH: 8
<212> TYPE: PRT
<213> ORGANISM: Artificial Sequence
<220> FEATURE:
<223> OTHER INFORMATION: CDR2

<400> SEQUENCE: 158

Ile Asn Ala Gly Asn Gly Asn Thr
1               5

<210> SEQ ID NO 159
<211> LENGTH: 5
<212> TYPE: PRT
<213> ORGANISM: Artificial Sequence
<220> FEATURE:
<223> OTHER INFORMATION: Heavy chain CDR3 Seq

<400> SEQUENCE: 159

Thr Arg Gly Asp Tyr
1               5

<210> SEQ ID NO 160
<211> LENGTH: 12
<212> TYPE: PRT
<213> ORGANISM: Artificial Sequence
<220> FEATURE:
<223> OTHER INFORMATION: Heavy chain CDR3 Seq

<400> SEQUENCE: 160

Ala Arg His Thr Ile Pro Pro Tyr Val Met Asp Tyr
1               5                   10

<210> SEQ ID NO 161
<211> LENGTH: 9
<212> TYPE: PRT
<213> ORGANISM: Artificial Sequence
<220> FEATURE:
<223> OTHER INFORMATION: Heavy chain CDR3 Seq

<400> SEQUENCE: 161

Ala Arg Asp Glu Gly Ile Tyr Gly Tyr
1               5

<210> SEQ ID NO 162
<211> LENGTH: 15
<212> TYPE: PRT
<213> ORGANISM: Artificial Sequence
<220> FEATURE:
<223> OTHER INFORMATION: Heavy chain CDR3 Seq

<400> SEQUENCE: 162

Ala Arg Gly Val Tyr Asn Tyr Gly Arg Val Trp Tyr Phe Asp Val
1               5                   10                  15

<210> SEQ ID NO 163
<211> LENGTH: 13
<212> TYPE: PRT
<213> ORGANISM: Artificial Sequence
<220> FEATURE:
<223> OTHER INFORMATION: Heavy chain CDR3 Seq

<400> SEQUENCE: 163

Ala Arg Arg Asp Tyr Asp Asn Tyr Val Pro Phe Ala Tyr
1               5                   10

```
<210> SEQ ID NO 164
<211> LENGTH: 11
<212> TYPE: PRT
<213> ORGANISM: Artificial Sequence
<220> FEATURE:
<223> OTHER INFORMATION: Heavy chain CDR3 Seq

<400> SEQUENCE: 164

Thr Gly Asp Tyr Glu Phe Gly Leu Phe Asp Tyr
1               5                   10

<210> SEQ ID NO 165
<211> LENGTH: 9
<212> TYPE: PRT
<213> ORGANISM: Artificial Sequence
<220> FEATURE:
<223> OTHER INFORMATION: Heavy chain CDR3 Seq

<400> SEQUENCE: 165

Ala Arg Leu Ser Gly Thr Phe Ala Tyr
1               5

<210> SEQ ID NO 166
<211> LENGTH: 8
<212> TYPE: PRT
<213> ORGANISM: Artificial Sequence
<220> FEATURE:
<223> OTHER INFORMATION: Heavy chain CDR3 Seq

<400> SEQUENCE: 166

Ala Ser Leu Lys Gly Ser Ala Tyr
1               5

<210> SEQ ID NO 167
<211> LENGTH: 10
<212> TYPE: PRT
<213> ORGANISM: Artificial Sequence
<220> FEATURE:
<223> OTHER INFORMATION: Heavy chain CDR3 Seq

<400> SEQUENCE: 167

Ala Arg Glu Gly Gly Tyr Tyr Phe Asp Tyr
1               5                   10

<210> SEQ ID NO 168
<211> LENGTH: 11
<212> TYPE: PRT
<213> ORGANISM: Artificial Sequence
<220> FEATURE:
<223> OTHER INFORMATION: Heavy chain CDR3 Seq

<400> SEQUENCE: 168

Ala Arg Asp Asn Gly His Asp Trp Phe Ala Tyr
1               5                   10

<210> SEQ ID NO 169
<211> LENGTH: 13
<212> TYPE: PRT
<213> ORGANISM: Artificial Sequence
<220> FEATURE:
<223> OTHER INFORMATION: Heavy chain CDR3 Seq

<400> SEQUENCE: 169

Ala Arg Arg Asp Tyr Gly Asn Tyr Val Pro Phe Ala Tyr
1               5                   10

<210> SEQ ID NO 170
```

```
<211> LENGTH: 12
<212> TYPE: PRT
<213> ORGANISM: Artificial Sequence
<220> FEATURE:
<223> OTHER INFORMATION: Heavy chain CDR3 Seq

<400> SEQUENCE: 170

Val Leu Asp Tyr Tyr Gly Tyr Ala Pro Phe Ala Tyr
1               5                   10

<210> SEQ ID NO 171
<211> LENGTH: 13
<212> TYPE: PRT
<213> ORGANISM: Artificial Sequence
<220> FEATURE:
<223> OTHER INFORMATION: Heavy chain CDR3 Seq

<400> SEQUENCE: 171

Ala Arg Asp Leu Tyr Tyr Ser His Gly Gly Phe Ala Tyr
1               5                   10

<210> SEQ ID NO 172
<211> LENGTH: 14
<212> TYPE: PRT
<213> ORGANISM: Artificial Sequence
<220> FEATURE:
<223> OTHER INFORMATION: Heavy chain CDR3 Seq

<400> SEQUENCE: 172

Ala Arg Val Asp Gly Tyr Leu Gln Gly Tyr Tyr Phe Gly Tyr
1               5                   10

<210> SEQ ID NO 173
<211> LENGTH: 12
<212> TYPE: PRT
<213> ORGANISM: Artificial Sequence
<220> FEATURE:
<223> OTHER INFORMATION: Heavy chain CDR3 Seq

<400> SEQUENCE: 173

Ala Arg Gly Arg Glu Gly Asn Gly Ala Met Asp Tyr
1               5                   10

<210> SEQ ID NO 174
<211> LENGTH: 15
<212> TYPE: PRT
<213> ORGANISM: Artificial Sequence
<220> FEATURE:
<223> OTHER INFORMATION: Heavy chain CDR3 Seq

<400> SEQUENCE: 174

Ala Arg Gln Glu Phe Tyr Tyr Gly Asn Tyr Asp Ala Met Asp Tyr
1               5                   10                  15

<210> SEQ ID NO 175
<211> LENGTH: 10
<212> TYPE: PRT
<213> ORGANISM: Artificial Sequence
<220> FEATURE:
<223> OTHER INFORMATION: Heavy chain CDR3 Seq

<400> SEQUENCE: 175

Ala Ser Gly Ile Leu Asn Val Met Asp Tyr
1               5                   10

<210> SEQ ID NO 176
<211> LENGTH: 11
```

```
<212> TYPE: PRT
<213> ORGANISM: Artificial Sequence
<220> FEATURE:
<223> OTHER INFORMATION: Heavy chain CDR3 Seq

<400> SEQUENCE: 176

Ala Arg Ala Thr Val Pro Ala Glu Ile Ala Tyr
1               5                   10

<210> SEQ ID NO 177
<211> LENGTH: 13
<212> TYPE: PRT
<213> ORGANISM: Artificial Sequence
<220> FEATURE:
<223> OTHER INFORMATION: Heavy chain CDR3 Seq

<400> SEQUENCE: 177

Ala Arg Trp Thr Gly Thr Gly Asp Tyr Ala Met Asp Tyr
1               5                   10

<210> SEQ ID NO 178
<211> LENGTH: 16
<212> TYPE: PRT
<213> ORGANISM: Artificial Sequence
<220> FEATURE:
<223> OTHER INFORMATION: Heavy chain CDR3 Seq

<400> SEQUENCE: 178

Ala Arg Ser Gly Leu Ile Tyr Asp Gly Tyr Tyr Ala Trp Phe Ala Tyr
1               5                   10                  15

<210> SEQ ID NO 179
<211> LENGTH: 9
<212> TYPE: PRT
<213> ORGANISM: Artificial Sequence
<220> FEATURE:
<223> OTHER INFORMATION: Kappa chain

<400> SEQUENCE: 179

Trp Gln Gly Thr His Phe Pro Trp Thr
1               5

<210> SEQ ID NO 180
<211> LENGTH: 9
<212> TYPE: PRT
<213> ORGANISM: Artificial Sequence
<220> FEATURE:
<223> OTHER INFORMATION: Kappa chain

<400> SEQUENCE: 180

Gln Asn Gly His Ser Phe Pro Tyr Thr
1               5

<210> SEQ ID NO 181
<211> LENGTH: 9
<212> TYPE: PRT
<213> ORGANISM: Artificial Sequence
<220> FEATURE:
<223> OTHER INFORMATION: Kappa chain

<400> SEQUENCE: 181

Gln Gln Tyr Tyr Ser Tyr Pro Arg Thr
1               5

<210> SEQ ID NO 182
<211> LENGTH: 9
<212> TYPE: PRT
```

```
<213> ORGANISM: Artificial Sequence
<220> FEATURE:
<223> OTHER INFORMATION: Kappa chain

<400> SEQUENCE: 182

Gln Gln Tyr Tyr Arg Tyr Pro Trp Thr
1               5

<210> SEQ ID NO 183
<211> LENGTH: 8
<212> TYPE: PRT
<213> ORGANISM: Artificial Sequence
<220> FEATURE:
<223> OTHER INFORMATION: Kappa chain

<400> SEQUENCE: 183

Gln Gln Tyr Tyr Asn Tyr Arg Thr
1               5

<210> SEQ ID NO 184
<211> LENGTH: 9
<212> TYPE: PRT
<213> ORGANISM: Artificial Sequence
<220> FEATURE:
<223> OTHER INFORMATION: Kappa chain

<400> SEQUENCE: 184

Met Gln His Leu Glu Tyr Pro Phe Thr
1               5

<210> SEQ ID NO 185
<211> LENGTH: 9
<212> TYPE: PRT
<213> ORGANISM: Artificial Sequence
<220> FEATURE:
<223> OTHER INFORMATION: Kappa chain

<400> SEQUENCE: 185

Gln Gln Tyr Tyr Ser Tyr Pro Trp Thr
1               5

<210> SEQ ID NO 186
<211> LENGTH: 8
<212> TYPE: PRT
<213> ORGANISM: Artificial Sequence
<220> FEATURE:
<223> OTHER INFORMATION: Kappa chain

<400> SEQUENCE: 186

Lys Gln Ser Tyr Asn Leu Leu Thr
1               5

<210> SEQ ID NO 187
<211> LENGTH: 8
<212> TYPE: PRT
<213> ORGANISM: Artificial Sequence
<220> FEATURE:
<223> OTHER INFORMATION: Kappa chain

<400> SEQUENCE: 187

Leu His Tyr Asp Asn Leu Trp Thr
1               5

<210> SEQ ID NO 188
<211> LENGTH: 8
<212> TYPE: PRT
<213> ORGANISM: Artificial Sequence
```

```
<220> FEATURE:
<223> OTHER INFORMATION: Kappa chain

<400> SEQUENCE: 188

Gln Gln Tyr Tyr Ser Tyr Arg Thr
1               5

<210> SEQ ID NO 189
<211> LENGTH: 8
<212> TYPE: PRT
<213> ORGANISM: Artificial Sequence
<220> FEATURE:
<223> OTHER INFORMATION: Kappa chain

<400> SEQUENCE: 189

Leu Gln Tyr Asp Asn Leu Leu Thr
1               5

<210> SEQ ID NO 190
<211> LENGTH: 9
<212> TYPE: PRT
<213> ORGANISM: Artificial Sequence
<220> FEATURE:
<223> OTHER INFORMATION: Kappa chain

<400> SEQUENCE: 190

Met Gln His Leu Glu Tyr Pro Tyr Thr
1               5

<210> SEQ ID NO 191
<211> LENGTH: 9
<212> TYPE: PRT
<213> ORGANISM: Artificial Sequence
<220> FEATURE:
<223> OTHER INFORMATION: Kappa chain

<400> SEQUENCE: 191

Gln Asn Asp His Ser Phe Pro Leu Thr
1               5

<210> SEQ ID NO 192
<211> LENGTH: 9
<212> TYPE: PRT
<213> ORGANISM: Artificial Sequence
<220> FEATURE:
<223> OTHER INFORMATION: Kappa chain

<400> SEQUENCE: 192

Ser Gln Ser Thr His Val Pro Pro Thr
1               5

<210> SEQ ID NO 193
<211> LENGTH: 9
<212> TYPE: PRT
<213> ORGANISM: Artificial Sequence
<220> FEATURE:
<223> OTHER INFORMATION: Kappa chain

<400> SEQUENCE: 193

Phe Gln Gly Ser His Val Pro Trp Thr
1               5

<210> SEQ ID NO 194
<211> LENGTH: 9
<212> TYPE: PRT
<213> ORGANISM: Artificial Sequence
<220> FEATURE:
```

<223> OTHER INFORMATION: Kappa chain

<400> SEQUENCE: 194

Trp Gln Gly Thr His Phe Pro Gln Thr
1               5

<210> SEQ ID NO 195
<211> LENGTH: 9
<212> TYPE: PRT
<213> ORGANISM: Artificial Sequence
<220> FEATURE:
<223> OTHER INFORMATION: Kappa chain

<400> SEQUENCE: 195

Gln Gln Trp Ser Ser Asn Pro Phe Thr
1               5

<210> SEQ ID NO 196
<211> LENGTH: 9
<212> TYPE: PRT
<213> ORGANISM: Artificial Sequence
<220> FEATURE:
<223> OTHER INFORMATION: Kappa chain

<400> SEQUENCE: 196

Gln Gln Trp Ser Ser Asn Pro Pro Thr
1               5

<210> SEQ ID NO 197
<211> LENGTH: 8
<212> TYPE: PRT
<213> ORGANISM: Artificial Sequence
<220> FEATURE:
<223> OTHER INFORMATION: Kappa chain

<400> SEQUENCE: 197

His Gln Trp Ser Ser Tyr Arg Thr
1               5

<210> SEQ ID NO 198
<211> LENGTH: 8
<212> TYPE: PRT
<213> ORGANISM: Artificial Sequence
<220> FEATURE:
<223> OTHER INFORMATION: Kappa chain

<400> SEQUENCE: 198

Lys Gln Ser Tyr Asn Leu Trp Thr
1               5

<210> SEQ ID NO 199
<211> LENGTH: 4
<212> TYPE: PRT
<213> ORGANISM: Artificial Sequence
<220> FEATURE:
<223> OTHER INFORMATION: FR4 initation region
<220> FEATURE:
<221> NAME/KEY: VARIANT
<222> LOCATION: 3
<223> OTHER INFORMATION: Xaa = any amino acid

<400> SEQUENCE: 199

Trp Gly Xaa Gly
1

<210> SEQ ID NO 200
<211> LENGTH: 3

```
<212> TYPE: PRT
<213> ORGANISM: Artificial Sequence
<220> FEATURE:
<223> OTHER INFORMATION: FR4 initation region

<400> SEQUENCE: 200

Gly Gln Gly
1

<210> SEQ ID NO 201
<211> LENGTH: 5
<212> TYPE: PRT
<213> ORGANISM: Artificial Sequence
<220> FEATURE:
<223> OTHER INFORMATION: characteristic sequences of Kappa and Lambda
      chains
<220> FEATURE:
<221> NAME/KEY: VARIANT
<222> LOCATION: 3
<223> OTHER INFORMATION: Xaa = any amino acid

<400> SEQUENCE: 201

Phe Gly Xaa Gly Thr
1               5
```